(12) United States Patent
Vilen et al.

(10) Patent No.: US 6,503,509 B1
(45) Date of Patent: Jan. 7, 2003

(54) METHOD FOR RECEPTOR DESENSITIZATION

(75) Inventors: Barbara J. Vilen, Chapel Hill, NC (US); John C. Cambier, Denver, CO (US)

(73) Assignee: National Jewish Medical & Research Center, Denver, CO (US)

( * ) Notice: Subject to any disclaimer, the term of this patent is extended or adjusted under 35 U.S.C. 154(b) by 0 days.

(21) Appl. No.: 09/513,024

(22) Filed: Feb. 25, 2000

Related U.S. Application Data

(60) Provisional application No. 60/121,954, filed on Feb. 25, 1999.

(51) Int. Cl.[7] .................. A61K 39/395; C07K 16/28; G01N 33/53
(52) U.S. Cl. ................. 424/153.1; 424/130.1; 424/136.1; 424/137.1; 424/141.1; 424/143.1; 424/144.1; 424/152.1; 424/172.1; 424/173.1; 530/387.1; 530/387.3; 530/388.1; 530/388.2; 530/388.22; 530/388.7; 530/388.73; 530/389.1; 530/389.6; 514/2; 514/885; 435/71
(58) Field of Search ................. 530/387.1, 388.1, 530/388.22, 388.7, 388.73, 385.1, 385.6, 387.3, 388.2; 424/130.1, 137.1, 141.1, 143.1, 144.1, 152.1, 153.1, 172.1, 173.1, 136.1; 514/2, 885; 435/325, 326, 375, 7.1

(56) References Cited

U.S. PATENT DOCUMENTS 6,103,713 A * 8/2000 Ways et al.

OTHER PUBLICATIONS

Immunobiology: The Immune System in Health and Disease, Sections 3–24 to 3–35 of Chapter 3, pp. 3–30 to 3–35, Janeway and Travers eds, 3rd edition, 1997, Current Biology Ltd/Garland Publishing Inc.*
Cambier et al. Proc. Natl. Acad. Sci. USA 1988, 85:6493–6497.*
Vilen et al. J. Immunol. 1997, 159:231–243.*
Nakamura et al. Int. J. Hematol. 1996, 64:39–46.*
Suzuki et al. Int Archs. Appl. Immunol. 1982, 69:296–301.*
Kahan Cur. Opin. Immunol. 1992 4:553–560.*
Bendall et al., *Mol. Immunol.,* 36:187–195 (1999).
Lanier et al., *Immunity,* 8:693–701 (1998).
Pani et al., *J. Exp. Med.,* 181:2077–2084 (1995).
Perussia et al., *J. Immunol.,* 130(5):2142–2148 (1983).
Farrar et al., *Biochim. Biophys. Acta,* 1377:F35–F78 (1998).
Weiner et al., *Cancer Immunol. Immunother.,* 42:141–150 (1996).
Cronin et al., *J. Immunol.,* 161:252–259 (1998).
Kishimoto et al., *J. Exp. Med.,* 182:1997–2006 (1995).
Lang et al., *J. Exp. Med.,* 184:1685–1697 (1996).
Vilen et al., *J. Immunol.,* 159:231–243 (1997).

* cited by examiner

*Primary Examiner*—Philip Gambel
*Assistant Examiner*—Jessica H. Roark
(74) *Attorney, Agent, or Firm*—Sheridan Ross P.C.

(57) ABSTRACT

Particular members of the multisubunit immune recognition receptor (MIRR) family of receptors, specifically, the B cell antigen receptor (BCR), the pre-B cell receptor (pre-BCR), the pro-B cell receptor (pro-BCR), Ig Fc receptors (FcR), and NK receptors, can be physically uncoupled from their associated transducers. The invention describes regulatory compounds and methods for mimicking such dissociation/destabilization for the purposes of receptor desensitization and for treatment of conditions in which receptor desensitization or alternatively, enhanced or prolonged receptor sensitization, is desirable. Compounds and methods for enhancing or prolonging receptor sensitization are also disclosed, as are methods for identifying regulatory compounds suitable for use in the present methods.

18 Claims, 11 Drawing Sheets

SEQUENCE LISTING

<160> NUMBER OF SEQ ID NOS: 1

<210> SEQ ID NO 1
<211> LENGTH: 22
<212> TYPE: PRT

```
<213> ORGANISM: Artificial/Unknown
<220> FEATURE:
<221> NAME/KEY: UNSURE
<222> LOCATION: (1)..(22)
<223> OTHER INFORMATION: mimetic

<400> SEQUENCE: 1

Cys Ala His Asp Trp Arg Ser Gly Phe Gly Gly Phe Gln His Leu Cys
1               5                   10                  15

Cys Gly Ala Ala Gly Ala
            20
```

METHOD FOR RECEPTOR DESENSITIZATION

CROSS-REFERENCE TO RELATED APPLICATIONS

This application claims priority under 35 U.S.C. § 119(e) from U.S. Provisional Application Ser. No. 60/121,954, filed Feb. 25, 1999, entitled "Product and Method for Treatment of Conditions Associated with Receptor-Desensitization." The entire disclosure of U.S. Provisional Application Ser. No. 60/121,954 is incorporated herein by reference in its entirety.

GOVERNMENT RIGHTS

This invention was made in part using government support under NIH Grant No. 20519, awarded by the National Institutes of Health. The government has certain rights to this invention.

FIELD OF THE INVENTION

This invention generally relates to a method and regulatory compound for desensitization of receptors. In particular, the invention relates to a method and regulatory compound for desensitization of B cell receptors, Fe receptors and NK receptors. The invention also relates to compounds and methods for sensitization of receptors.

BACKGROUND OF THE INVENTION

The B cell antigen receptor complex is composed of membrane immunoglobulin noncovalently associated with heterodimers of Ig-α and Ig-β. These signal transducing subunits contain a conserved ITAM motif (immunoreceptortyrosine-based activation motif) required for signal transduction (Cambier, 1995). Aggregation of the BCR by multivalent antigen initiates transphosphorylation of the Ig-α and Ig-β ITAM motifs and activation of receptor-associated kinases (for review see DeFranco, 1997; Kim et al., 1993; Kurosaki, 1997). Phosphorylated ITAMs recruit additional effectors such as PI3-K, PLC-γ and members of the Ras/MAPK pathway. These signaling events are responsible for B cell proliferation, and increased expression of activation markers such as MHC class II and CD86, that are required to prime the B cell for subsequent interactions with $T_h$ cells.

The B cell repertoire is finely tuned to contain maximal receptor diversity in the absence of autoreactivity. Autoreactive clones are eliminated by processes including clonal deletion by apoptosis or receptor editing, and anergy (Goodnow et al., 1988; Hartley et al., 1993; Hertz and Nemazee, 1997; Nemazee and Burki, 1989; Rathmnell et al., 1996). In the latter case, autospecific cells persist but are unresponsive to antigen. The molecular mechanisms underlying B cell unresponsiveness have been studied in BCR transgenic mice and in several in vitro models of receptor desensitization (Brunswick et al., 1994; Cambier et al., 1988; Cambier et al., 1990, Erikson et al., 1991; Gay et al., 1993; Nemazee and Burki, 1989; Okamoto et al., 1992; Vilen et al., 1997). Studies in the HEL/anti-HEL double transgenic mouse have shown that B cells tolerant to self-antigen exhibit reduced cell surface expression of IgM, are no longer capable of antigen-induced CD86 expression, and are sensitive to Fas mediated apoptosis (Goodnow etal., 1989; Ho et al., 1994; Rathmell et al., 1996). In a number of these models, receptor desensitization is characterized by the inability of antigen to elicit tyrosine phosphorylation or renewed $Ca^{2+}$ mobilization despite the continued expression of antigen binding receptors.

Recently, disruption of receptor proximal signaling events have been studied in desensitized B cells (Cooke et al., 1994; Vilen et al., 1997). Results from these studies reveal a lack of antigen induced phosphorylation and activation of receptor associated kinases such as Lyn, Blk, and Syk. Johnson et al. showed that receptor-associated kinases could be activated by exposure to doubly phosphorylated ITAM peptides, suggesting that the failure of desensitized receptors to activate signaling pathways was not due to a defect intrinsic to the kinase, but rather reflected a defect at the level of the receptor and its ability to couple to Lyn (Johnson et al., 1995). Johnson et al. hypothesize that receptor unresponsiveness may be due to an uncoupling of Lyn from an otherwise intact mIg/Igαβ complex, or alternatively, a result of excessive phosphotyrosine phosphatase activities at the receptor.

Despite considerable research in this area, previous investigators have failed to teach or suggest the molecular event that the present inventors have shown to be responsible for maintaining the unresponsive phenotype of desensitized receptors. Therefore, prior to the present invention, therapeutic compounds which specifically target this molecular event have not been identified.

A wide variety of medical treatments require regulation of the immune response in a patient. Such treatments include, for example, vaccinations, treatments for autoimmune diseases, immunodeficiency diseases, immunoproliferative diseases, and treatments involving the transplantation of organs and skin. Traditional reagents and methods used to regulate a subject's immune response often results in unwanted side effects. For example, immunosuppressive reagents such as cyclosporin A, azathioprine, and prednisone are used to suppress the immune system of a patient with an autoimmune disease or patients receiving transplants. Such reagents, however, suppress a patient's entire immune response, thereby crippling the ability of the patient to mount an immune response against infectious agents not involved in the original disease. Due to such harmful side effects and the medical importance of immune regulation, reagents and methods to regulate specific parts of the immune system have been the subject of study for many years.

The present invention can be used to overcome traditional problems with immunoregulatory reagents by targeting specific cells and immune receptors in vivo.

SUMMARY OF THE INVENTION

The present invention generally relates to methods and compounds for desensitizing a receptor selected from the group consisting of a B cell antigen receptor (BCR), a pro-B cell receptor (pro-BCR), a pre-B cell receptor (pre-BCR), immunoglobulin Fc receptor (FcR) and natural killer (NK) cell receptor. Such a method includes the step of contacting a compound with such a receptor that has an extracellular ligand binding component and a transducer component, wherein contact with the compound: (1) causes a dissociation of the extracellular ligand binding component from the transducer component when the two components are associated prior to contact with the compound, and/or (2) inhibits association of the extracellular ligand binding component with the transducer component when the two components are dissociated prior to contact with the compound, thereby desensitizing the receptor.

The present invention also relates to a method and compounds for sensitizing or prolonging/enhancing sensitization of a receptor selected from the group consisting of BCR, pro-BCR, pre-BCR, FcR and NK receptor. Such a method includes the step of contacting a compound with such a receptor that has an extracellular ligand binding component and a transducer component, wherein the compound: (1) causes the extracellular ligand binding component to associate with the transducer component when the two components are not associated with each other prior to contact by the compound; and/or (2) prolongs or enhances the time over which the extracellular ligand binding component is associated with the transducer component when the components are associated prior to contact by the compound, thereby sensitizing the receptor.

More particularly, one embodiment of the present invention relates to a method to desensitize a B cell antigen receptor, and preferably, by selectively desensitizing a B cell antigen receptor which binds to a specific antigen. Such a method is useful for treating any B cell-related disorder in which desensitization of the B cell antigen receptor would provide a therapeutic benefit, alone or in conjunction with another treatment. Such a method is also useful for research and diagnostic assays, and for screening putative regulatory compounds. Such method includes the step of contacting a regulatory compound with a B cell antigen receptor that has an mIg component and a transducer component including Igα and/or Igβ, wherein contact with the compound: (1) causes a dissociation of the mIg component from the transducer component when the two components are associated prior to contact with the compound, and/or (2) inhibits association of the mIg component with the transducer component when the two components are dissociated prior to contact with the compound, thereby desensitizing the B cell antigen receptor. The mIg component can be either IgD or IgM. A B cell-disorder that can be treated by the present method can include, but is not limited to, autoimmune disease (e.g., rheumatoid arthritis or systemic lupus erythematosus), malignancies and transplantation. A particularly preferred disorder to treat with the method of the present invention is an autoimmune disease. Preferably, the compound selectively targets a BCR having a particular antigen specificity, such as a B cell antigen receptor which specifically binds to an autoantigen. Such a method is advantageous in that functions of normal or desirable B cells can be left intact, while functions of abnormal or undesirable B cells can be inhibited.

Another embodiment of the present invention relates to a method to sensitize or prolong/enhance sensitization of a BCR. Such a method is useful, for example, for increasing or inducing a B cell response to a given antigen or antigens, and can be used in a vaccine or adjuvant system. In one embodiment, the method includes the step of contacting a compound with a B cell antigen receptor that has an mIg component and a transducer component including Igα and Igβ, wherein the compound: (1) causes the mIg component to associate with the transducer component when the components are not associated with each other prior to contact by the compound; and/or (2) prolongs or enhances the time over which the mIg component is associated with the transducer component when the components are associated prior to contact by the compound, thereby enhancing sensitization of the B cell antigen receptor for treatment of the disorder. In one embodiment of this method, an additional factor can be contacted with the B cell antigen receptor, such as an antigen or other factor which enhances vaccination against a given antigen or enhancement of the B cell antigen response.

One embodiment of the present invention relates to a method to treat autoimmune disease, including the step of contacting a compound with an autoreactive B cell antigen receptor that has an mIg component associated with a transducer component including Igα and Igβ, wherein contact with the compound: (1) causes a dissociation of the mIg component from the transducer component when the two components are associated prior to contact with the compound, and/or (2) inhibits association of the mIg component with the transducer component when the two components are dissociated prior to contact with the compound, thereby desensitizing the B cell antigen receptor for treatment of an autoimmune disease.

Another embodiment of the present invention relates to a method desensitize an Ig Fc receptor (FcR). Such a method is useful for treating any disorder in which desensitization of an FcR, and particularly, a specific FcR, would provide a therapeutic benefit, alone or in conjunction with another treatment. Such a method is also useful for research and diagnostic assays, and for screening putative regulatory compounds. Such disorders include, but are not limited to, an allergic disorder; and disorders related to inflammatory responses including antibody-dependent cell-mediated cytotoxicity, release of inflammatory mediators and regulation of antibody production, and more particularly include, but are not limited to, thrombocytopenia purpura, rheumatoid arthritis, systemic lupus erythematosus, type II and type III hypersensitivity reactions, and allergic inflammation. The method includes the step of contacting a compound with an Fc receptor that has an α receptor component and a transducer component, wherein contact with the compound: (1) causes a dissociation of the α receptor component from the transducer component when the two components are associated prior to contact with the compound, and/or (2) inhibits association of the α receptor component with the transducer component when the two components are dissociated prior to contact with the compound, thereby desensitizing the Fc receptor.

Another embodiment of the present invention relates to a method to treat allergic disorders, including the step of contacting a compound with an FcεRI receptor that has an α receptor component and a transducer β/γ component, wherein contact with the compound: (1) causes a dissociation of the α receptor component from the transducer component when the two components are associated prior to contact with the compound, and/or (2) inhibits association of the α receptor component with the transducer component when the two components are dissociated prior to contact with the compound, thereby desensitizing the FcεRI receptor for treatment of the allergic disorder.

Another embodiment of the present invention relates to a method to identify compounds useful for desensitizing a receptor, including the steps of: (1) providing an assay system including a receptor selected from a B cell antigen receptor, a pro-B cell receptor, a pre-B cell receptor or an Fc receptor, wherein the receptor includes an extracellular ligand binding component and at least one transducer component, and wherein the extracellular ligand binding component is associated with the transducer component; (2) contacting the receptor with a compound to be evaluated; and, (3) determining whether the compound, when contacted with the receptor, is capable of causing the extracellular ligand binding component to dissociate from the transducer component. In the case of a B cell antigen receptor, the extracellular ligand binding component is mIg and the transducer components are Igα and Igβ. In the case of an FcR receptor, the extracellular ligand binding receptor is typically the α receptor chain, and the transducer component varies depending on the specific FcR, as is known in the art. For the FcεRI, the transducer components are β and γ chains.

Yet another embodiment of the present invention relates to a method to identify compounds useful for desensitizing a receptor, including the steps of: (1) providing an assay system including a receptor selected from a B cell antigen receptor or an Fc receptor, wherein the receptor includes an extracellular ligand binding component and at least one transducer component, and wherein the extracellular ligand binding component is not associated with the transducer component; (2) contacting the receptor with a compound to be evaluated; and, (3) determining whether the compound, when contacted with the receptor, is capable of inhibiting the extracellular ligand binding component from associating with the transducer component.

The above methods can include cell-based assays and non-cell based assays. Compounds identified by the above methods are useful for treating a variety of B cell and FcR-associated disorders, including autoimmune disease and allergic disorders. The methods of desensitizing/sensitizing a receptor and compounds useful in such methods can be performed/used in vivo, in vitro, and/or ex vivo. In addition, the above-described regulatory compounds, including those identified by the present method, can be used in a therapeutic composition and in a method of treatment or desensitization of the present invention.

Yet another embodiment of the present invention relates to a compound useful for treating a condition selected from the group consisting of a B cell-associated disorder and an FcR-associated disorder. Such a compound is characterized by its ability to: (1) cause a dissociation of an extracellular ligand binding component from a transducer component in a B cell antigen receptor or an Fc receptor when the two components are associated prior to contact with the compound, and/or (2) inhibit association of the extracellular ligand binding component with the transducer component when the two components are dissociated prior to contact with the compound, thereby desensitizing the receptor. In a preferred embodiment, the compound is selected from an antibody, a peptide, or a mimetope thereof. In one embodiment, the compound is an antibody. Such an antibody can be a monovalent antibody, a divalent antibody, or a bi-specific antibody.

Another embodiment of the present invention relates to an isolated antibody which selectively binds to a BCR, wherein the antibody, upon binding to such a BCR having an mIg component associated with Igα and Igβ components, is capable of inducing the mIg component to dissociate from the Igα and Igβ components, thereby desensitizing the BCR. In one embodiment, the BCR is expressed by a B cell. Such an antibody can be used in a method of the present invention to desensitize a B cell antigen receptor.

Another embodiment of the present invention relates to an isolated antibody which selectively binds to an FcR, wherein the antibody, upon binding to such an FcR that has an α receptor component associated with at least one transducer component, is capable of inducing the α receptor component to dissociate from the transducer component, thereby desensitizing the FcR. In one embodiment, the FcR is FcεRI, and the transducer components are β and γ chains. In another embodiment, the FCεRI is expressed by a mast cell, a basophil or an eosinophil. Such an antibody can be used in a method of the present invention to desensitize an Fc receptor.

All patents and publications referenced herein are incorporated by reference in their entireties.

BRIEF DESCRIPTION OF THE FIGURES

The patent or application file contains at least one drawing executed color. Copies of this patent or patent application with color drawing will be provided by the Office upon request and payment of the necessary fee.

DETAILED DESCRIPTION OF THE INVENTION

Figure 1:
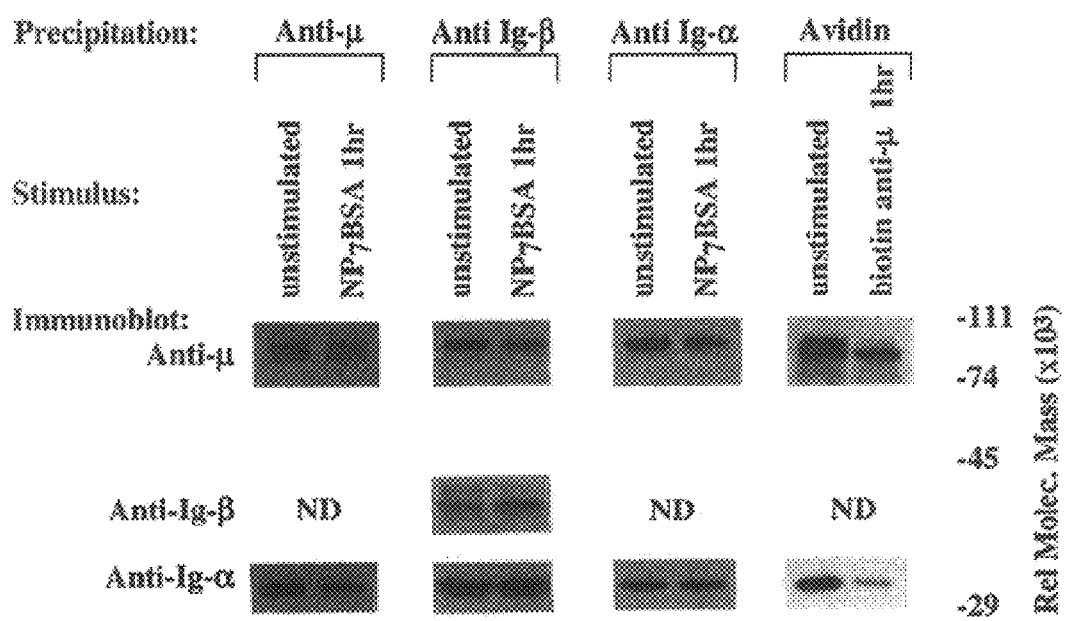
FIG. 1 is a digitized image of an immunoblot showing a comparative analysis of mIg-Ig-α/Ig-β association in unstimulated K46μ cells, cells stimulated 1 hour with NP$_7$BSA, or cells stimulated 1 hour with biotinylated b-7-6.

B cell antigen receptor (BCR) ligation leads to receptor desensitization wherein BCR remain competent to bind antigen yet fail to transduce signals. Desensitized BCR exhibit a defect at the most proximal level of signal transduction, consistent with failed transmission of signals through the receptor complex. The present inventors have discovered that antigen stimulation leads to dissociation or destabilization of the BCR reflected by inability to coimmunoprecipitate Ig-α/Ig-β with mIg. This destabilization is temporally correlated with desensitization and occurs in BCR containing mIgM and mIgD. Induction of BCR destabilization requires tyrosine kinase activation, but is not induced by phosphatase inhibitors. BCR destabilization occurs at the cell surface and "dissociated" Ig-α/Ig-β complexes remain responsive to anti-IG-β stimulation, indicating that mIg-transducer uncoupling mediates receptor desensitization. More particularly, the present inventors have shown that upon binding of moderate to low affinity antigen, the Ig-α/Ig-β subunits of the BCR become destabilized or physically dissociated from mIg. This event requires specific activation of the BCR signaling cascade. Most interestingly, although desensitized receptors fail to respond to receptor ligation, the Ig-α/Ig-β complex retains signaling function if aggregated, indicating that transducer dissociation from mIg mediates the unresponsive state.

The present invention generally relates to the discovery that particular members of the multisubunit immune recognition receptor (MIRR) family of receptors, specifically, the B cell antigen receptor (BCR), the pre-B cell receptor (pre-BCR), the pro-B cell receptor (pro-BCR), Ig Fc receptors (FcR), and NK receptors, can be physically uncoupled from their associated transducers. One embodiment of the present invention relates to a method to desensitize a receptor selected from the group of a B cell antigen receptor, a pro-B cell receptor, a pre-B cell receptor and an Ig Fc receptor. Another embodiment of the present invention relates to a method to desensitize a receptor selected from the group of a B cell antigen receptor, a pro-B cell receptor, a pre-B cell receptor, an Ig Fe receptor and an NK receptor. The method includes the steps of contacting such a receptor with a regulatory compound, wherein the receptor has a transducer component and an extracellular ligand binding component. The regulatory compound: (1) causes a dissociation of the extracellular ligand binding component from the transducer component when the components are associated with each other prior to contact with the compound; or (2) inhibits association of the extracellular ligand binding component with the transducer component when the components are dissociated from each other prior to contact with the compound.

In the case of the B cell antigen receptor (BCR), the present inventors have discovered that desensitization of the receptor involves an uncoupling of Ig-α/β from mIg. The present inventors provide evidence herein that uncoupling of the BCR transducer (Ig-α/β) from the antigen binding receptor (mIg heavy and light chains) is responsible for the desensitized phenotype exhibited by B cells following antigen stimulation. The present inventors' discovery regarding the BCR has led to the additional conclusion that the FcR, and particularly, FcεRI will, upon desensitization of this receptor in mast cells, exhibit uncoupling of the transducer component (e.g., β/γ subunit for FcεRI) from the receptor. This discovery has tremendous therapeutic potential in that one could intervene and prevent signaling through these receptors. In the case of mast cell degranulation, this mechanism of desensitization can be manipulated to treat allergic disorders, for example. In the case of the BCR, such a mechanism can be manipulated for the treatment of autoimmune disease, for example. Additionally, using the method of the present invention, the extracellular ligand binding component of the natural killer (NK) cell receptor, referred to as KIRDL, can be desensitized by affecting the association of the KIRDL with its transducer, referred to as DAP12.

According to the present invention, a transducer, or transducer component, is a component (i.e., portion, constituent, element) of a receptor, and typically one or more chains of a receptor, which transduces a signal from the receptor to other signal transduction molecules inside a cell when the receptor is ligated by its ligand. More specifically, by associating with an extracellular ligand binding component, a transducer component allows the extracellular ligand binding component(s) of a receptor to associate indirectly with cytosolic enzymes that provide the means of intracellular signaling when the extracellular ligand binding component is bound by its ligand, or an equivalent stimulus. In B cells, including pro-B, pre-B, immature and mature B cells, the transducer component is typically an Igα and an Igβ chain, which form a dimer. For Fc receptors, a transducer component is typically one or more chains associated with an α chain of the receptor, which are sufficient to associate with cytosolic enzymes that provide the means of intracellular signaling when the extracellular ligand binding component is bound by its ligand, or an equivalent stimulus. For example, transducer components of an FcεRI include a β chain and a dimer of γ chain. An FcγRI, FcγRIIa, FcγRIIc, FcγRIII and FcαR's typically have a γ chain dimer transducer component. An NK cell transducer component is DAP12. As used herein, a transducer component can include naturally occurring transducer components or any portion thereof that interacts with an extracellular ligand binding component as described herein and that is sufficient to transduce a signal from the receptor upon appropriate stimulation.

According to the present invention, an extracellular ligand binding component is a component (i.e., portion, constituent, element) of a receptor, and typically one or more chains of a receptor, at least a portion of which extends out of the cell surface (i.e., is extracellular) and which is the portion of a receptor which binds to a ligand. The extracellular ligand binding component may also have a transmembrane and a cytoplasmic portion. Typically, the extracellular ligand binding component is not a component of the receptor which is responsible for intracellular signaling by the receptor. By way of example, the extracellular ligand binding component of an immature B cell is a mIgM, which includes the antigen binding portion of the B cell antigen receptor; the extracellular ligand binding component of receptors on a mature, naive B cell includes both mIgM and mIgD. For Fc receptors, the extracellular ligand binding component is typically an α chain of the receptor, and is the portion of the receptor which binds the Fc region of an immunoglobulin. For NK receptors, the extracellular ligand binding component is referred to as KIRDL. As used herein, an extracellular ligand binding component can include a naturally occurring extracellular ligand binding component or any portion of thereof that interacts with a transducer component as described herein and/or that is sufficient to bind to a ligand for the receptor or to an equivalent stimulus.

As discussed above, B cell receptors which are suitable targets for the methods of the present invention include B cell antigen receptors (e.g., on immature or mature B cells), pro-B cell receptors, and pre-B cell receptors. A pro-B cell appears during B cell differentiation before immunoglobulin gene rearrangement has begun, and is identified by surface markers characteristic of B cells, including extracellular components (e.g., calnexin) that can associate with an Igα-Igβ transducer component. In late pro-B cell development, a $V_H$ segment becomes joined to the $DJ_H$ segment (discussed in detail below), producing a pre-B cell that expresses both low levels of surface and high levels of cytoplasmic μ heavy chain. An immature B cell expresses both light chains and μ heavy chains as surface IgM molecules (i.e., mIgM). Finally, mature, naive B cells express both mIgM and mIgD. The cytoplasmic tail of these transmembrane B cell receptor components, such components generally referred to herein as an extracellular ligand binding component, consists of only a few amino acids and is too short to interact with the proteins required for intracellular signaling. Transmission of signals instead depends on two other chains associated with the extracellular ligand binding component. These transducer components are called Igα and Igβ. The transducer components allow the extracellular ligand binding components of the receptor to associate with cytosolic enzymes that provide the means of intracellular signaling when B cells come into contact with antigen.

According to the present invention, reference to "B cells" or "B lymphocytes" includes splenic B cells, lymph node B cells, myeloma cells, peripheral blood B cells, bone marrow B cells and hybridoma cells. Hybridoma cells refer to hybrid cell lines comprising myeloma cells (tumor cells capable of being maintained in tissue culture but do not produce immunoglobulin) fused with, for example, a spleen cell capable of producing an immunoglobulin molecule. Reference to a "B cell antigen receptor" or "BCR" is intended to reference the B cell antigen receptor, which includes a membrane immunoglobulin (mIg) antigen binding component (i.e., an extracellular ligand binding component), or a biologically active portion thereof (i.e, a portion capable of binding a ligand and/or capable of associating with a transducer component), and transducer Ig-α and Ig-β components, or biologically active portions thereof (i.e., a portion capable of transducing an intracellular signal and/or capable of associating with an extracellular ligand binding portion).

According to the present invention, Fc receptors include Fc gamma receptors (FcγR) which bind gamma immunoglobulin (IgG), Fc epsilon receptors (FcεR) which bind epsilon immunoglobulin (IgE), Fc alpha receptors (FcαR) which bind alpha immunoglobulin (IgA). FcγR include, FcγRI, which is a high a affinity receptor for IgG; FcγRII, which are low affinity receptors for IgG that avidly bind to aggregates immune complexes; and FcγRIII, which are low affinity receptors that bind to immune complexes.

According to the present invention, NK receptors include an extracellular ligand binding component, KIRDL, and a transducer component, DAP12.

According to the present invention, reference to an "Fc receptor" or "FcR" refers to one or more members of a family of highly related receptors that specifically bind to the Fc portion of immunoglobulin (Ig). FcR can also be referred to herein as immunoglobulin Fc receptors or Ig Fc receptors (Ig FcR). These receptors have major roles in normal immunity and resistance to infection and provide the humoral immune system with a cellular effector arm. Receptors have been defined for each of the immunoglobulin classes and as such are defined by the class of Ig of which they bind (i.e. Fc gamma receptor (FcγR) bind gamma immunoglobulin (IgG), Fc epsilon receptor (FcεR) bind epsilon immunoglobulin (IgE), Fc alpha receptor (FcαR) bind alpha immunoglobulin (IgA)). Among the FcγR receptors, three subfamily members have been defined; FcγRI, which is a high a affinity receptor for IgG; FcγRII, which are low affinity receptors for IgG that avidly bind to aggregates immune complexes; and FcγRIII, which are low affinity receptors that bind to immune complexes. These receptors are highly related structurally but perform different functions.

FcγR are expressed on most hematopoietic cells, and through the binding of IgG play a key role in homeostasis of the immune system and host protection against infection. FcγRII is a low affinity receptor for IgG that essentially binds only to IgG immune complexes and is expressed on a variety of cell types including, for example monocytes, macrophages, neutrophils, eosinophils, platelets and B lymphocytes. FcγRII is involved in various immune and inflammatory responses including antibody-dependent cell-mediated cytotoxicity, clearance of immune complexes, release of inflammatory mediators and regulation of antibody production. The binding of IgG to an FcγR can lead to disease indications that involve regulation by FcγR. For example, the autoimmune disease thrombocytopenia purpura involves tissue (platelet) damage resulting from FcγR-dependent IgG immune complex activation of platelets or their destruction by FcγR+ phagocytes. In addition, various inflammatory disease are known to involve IgG immune complexes (e.g. rheumatoid arthritis, systemic lupus erythematosus), including type II and type III hypersensitivity reactions. Type II and type III hypersensitivity reactions are mediated by IgG, which can activate either complement-mediated or phagocytic effector mechanisms, leading to tissue damage.

FCεR are expressed on mast cells, basophils and eosinophils, and through the binding of IgE, trigger an inflammatory immune response which is primarily due to the release of inflammatory mediators upon degranulation of the mast cell (e.g., histamine and serotonin). Release of these mediators causes localized vascular permeability and increase in fluids in the local tissues, including an influx of polymorphonuclear cells into the site. Thus, binding of IgE to an FcεRI can lead to disease indications that involve discharge of fluids from the gut and increased mucus secretion and bronchial contraction, such indications typically being associated with diseases involving allergic inflammation.

Natural killer (NK) cells are identified by their ability to kill certain lymphoid tumor cell lines in vitro without the need for prior immunization or activation. In vivo, NK cells play a role in innate immunity by providing early protection from a range of pathogens. Such mechanisms can hold infection in check during its early phases while the adaptive immune response is developing.

According to the present invention, "receptor desensitization" refers to a state of "unresponsiveness" of a receptor, or in other words, a state wherein the receptor remains competent to bind its ligand, yet fails, or has a reduced ability, to transduce signals. Although a desensitized receptor fails to respond to receptor ligation by transducing an intracellular signal, the present inventors have discovered that the transducer component retains signaling function if aggregated, indicating that transducer dissociation from the extracellular ligand binding component mediates the unresponsive state. Receptor desensitization is characterized, for example, by the inability of ligand to elicit tyrosine phosphorylation or renewed $Ca^{2+}$ mobilization in a cell expressing the receptor, despite the continued expression of ligand binding receptors. More particularly, a receptor desensitization occurs according to the present invention by a physical uncoupling, dissociation or destabilization, of the extracellular ligand binding component of the receptor from the transducer component of the receptor.

According to the method of the present invention, a receptor is contacted with a regulatory compound. As used herein, a regulatory compound can be any compound which, when contacted with a receptor according to the present invention: (1) causes a dissociation of the extracellular ligand binding component from the transducer component when the components are associated with each other (i.e., prior to contact with the compound); or (2) inhibits association of the extracellular ligand binding component with the transducer component when the components are dissociated from each other (i.e., prior to contact with the compound). A regulatory compound is a compound that mimics the desensitized state through inducing uncoupling of the transducers of these receptors. A regulatory compound for desensitization of a receptor according to the present invention therefore preferably does not stimulate the receptor upon contact with the receptor, or has substantially reduced stimulatory ability as compared to a natural ligand or its equivalent stimulus, for example. Such compounds are useful in the method of desensitizing a receptor of the present invention. Without being bound by theory, the present inventors believe that the uncoupling of a receptor from its transducer components may be due to a mechanism that includes phosphorylation of serine/threonine/tyrosine residues in TM (transmembrane) domain of the extracellular ligand binding component, such as $\mu$ (i.e., mIg) in the BCR. In the BCR, this phosphorylation-mediated mechanism is supported by both the rapidity of uncoupling/dissociation and the requirement for kinase activation in BCR destabilization. This may seem somewhat counterintuitive given the $\mu$TM would be "shielded" from kinase by its location in lipid bilayer. However, the definition of "TM" residues versus "cytoplasmic" residues is based on protein algorithms, and although Kyle/Doolittle define this as lipid embedded, the present inventors believe that these residues can be cytoplasmic under certain conditions (i.e., antigen binding). The present inventors believe that the region may be kinase accessible only following antigen binding since: 1) the receptors are initially coupled prior to antigen binding; and 2) only antigen or anti-idiotype, but not anti-Ig-$\beta$, anti-Ig-$\alpha$, anti-$\lambda$ or pervanadate can induce dissociation. This suggests an antigen induced conformational change that renders the target residue accessible to kinase located in the cytoplasm. Additionally, and without being bound by theory, the present inventors believe that a portion of the extracellular portion of a BCR may be associating with the Ig-$\alpha$ or Ig-$\beta$ chain prior to antigen binding, such region moving to become accessible to phosphorylation subsequent to antigen binding. An equivalent scenario applies to Fc receptors.

Therefore, in one embodiment of the present invention, a regulatory compound useful in the present invention preferably binds to a site on a receptor which includes the antigen binding site or a site that is extracellular prior to antigen/ligand binding, and which is associated with a transducer component of the receptor and/or is phosphorylated in the cytoplasmic region subsequent to antigen/ligand binding. Suitable sites include a site on the transducer component or on the extracellular ligand binding component. Preferably, the site is on the transducer component. When the site is on the extracellular ligand binding component, it is preferably to target a site that is unique to the membrane form of the extracellular ligand binding site, or to target this component in receptors which have low levels of circulating (soluble) receptor. Alternate sites to target include transmembrane and/or cytoplasmic sites which are involved in association of the receptor components and or is phosphorylated upon antigen/ligand binding. Such transmembrane or cytoplasmic sites may be made available using delivery vehicles which are known in the art, and include liposomes and viral delivery systems. When the method of the present invention is directed to desensitization of the receptor, the target site is preferably a site other than the antigen/ligand binding site, to minimize signal induction through the receptor prior to dissociation of the components, although the antigen binding site is not excluded as a target site. When the method of the present invention is directed to sensitization of the receptor, the target site preferably includes the antigen/ligand binding site, to optimize, enhance and/or prolong signal induction through the receptor.

In a preferred embodiment, the regulatory compound binds to a site which prevents or inhibits association of the extracellular ligand binding component with the transducer component when the components are dissociated from each other. In one embodiment, the regulatory compound selectively binds to a portion of the transducer component that contacts a portion of the extracellular ligand binding component when the receptor is bound by its natural ligand. Therefore, the regulatory compound prevents or inhibits contact of the transducer component with the extracellular ligand binding component. In another embodiment, the regulatory compound selectively binds to a portion of the transducer component which contacts a portion of the extracellular ligand binding component that is phosphorylated when the receptor is bound by its natural ligand. Therefore, the regulatory compound prevents or inhibits phosphorylation of the extracellular ligand binding component. In one embodiment, when the receptor is a B cell antigen receptor, the regulatory compound binds to a portion of an Ig$\alpha$-Ig$\beta$ dimer which prevents or inhibits association of the dimer with a mIg.

It is to be noted that while the above discussion pertains primarily to compounds for desensitizing a receptor, with regard to compounds that prolong or enhance sensitization of the receptor, the target sites for binding can be similar or the same, however, the compounds are selected on the basis of being capable of preventing or inhibiting dissociation of the receptor components, causing the receptor components to associate, and/or prolonging the time during which the receptor components are associated subsequent to stimulation, such as by the receptor ligand.

Regulatory compounds as referred to herein include, for example, compounds that are products of rational drug design, natural products and compounds having partially defined signal transduction regulatory properties. A putative compound can be a protein-based compound, a carbohydrate-based compound, a lipid-based compound, a nucleic acid-based compound, a natural organic compound, a synthetically derived organic compound, an anti-idiotypic antibody and/or catalytic antibody, or fragments thereof. In one embodiment, a regulatory compound suitable for use in the present invention can include an antibody (i.e., an immunoglobulin), a peptide, or a mimetope thereof. In one embodiment, the regulatory compound is an antibody.

A naturally-occurring immunoglobulin molecule is a plasma protein comprising immunoglobulin domains. An immunoglobulin molecule comprises two types of chains. One type of chain is referred to as the heavy or H chain and the other is referred to as the light or L chain. The two chains are present in an equimolar ratio, and each immunoglobulin molecule has at least two H chains and at least two L chains. The two H chains are linked together by disulfide bonds and each H chain is linked to a L chain by a disulfide bond. There are only two types of L chains referred to as lambda ($\lambda$) and kappa ($\kappa$) chains. In contrast, there are five major H chain classes referred to as isotypes. The five classes include immunoglobulin M (IgM or $\mu$), immunoglobulin D (IgD or $\delta$), immunoglobulin G (IgG or $\lambda$), immunoglobulin A (IgA or $\alpha$), and immunoglobulin E (IgE or $\epsilon$). The distinctive characteristics between such isotypes are defined by the constant domain of the immunoglobulin and are discussed in detail below. Human immunoglobulin molecules comprise nine isotypes, IgM, IgD, IgE, four subclasses of IgG including IgG1 (γ1), IgG2 (γ2), IgG3 (γ3) and IgG4 (γ4), and two subclasses of IgA including IgA1 (α1) and IgA2 (α2).

Each H or L chain of an immunoglobulin molecule comprises two domains referred to as L chain variable regions ($V_L$ regions) and L chain C regions ($C_L$), and H chain V regions ($V_H$ regions) and H chain C regions ($C_L$ regions). A complete $C_H$ region comprises a CH1, CH2, CH3 domain and a hinge region. Together, one H chain and one L chain form an arm of an immunoglobulin molecule having an immunoglobulin V region. A complete immunoglobulin molecule comprises two arms, di-sulfide bonded by the H chain C regions of each arm. Thus, each arm of an immunoglobulin comprises two domains referred to as a $V_{H+L}$ region, and a $C_{H+L}$ region. As used herein, the term "variable region" or "V region" refers to a $V_{H+L}$ region, a $V_L$ region or a $V_H$ region. Also as used herein, the term "constant region" or "C region" refers to a $C_{H+L}$ region, a $C_L$ region or a $C_H$ region.

Limited digestion of an immunoglobulin with a protease produces two fragments. An antigen binding protease fragment is referred to as an Fab or an F(ab')$_2$ fragment. A protease fragment lacking the ability to bind to antigen is referred to as an Fc fragment. An Fab fragment comprises one arm of an immunoglobulin molecule containing a L chain ($V_L$ region+$C_L$ region) paired with the $V_H$ region and a portion of the $C_H$ region (CH1 domain). An F(ab')$_2$ fragment corresponds to two di-sulfide bonded arms of an immunoglobulin molecule, each arm containing a L chain ($V_L$ region+$C_L$ region) paired with a $V_H$ region and a CH1 domain.

A $C_H$ region defines the isotype of an immunoglobulin and confers different functional characteristics depending upon the isotype. For example, $\mu C$ regions enable the formation of pentameric aggregates of IgM molecules and $\alpha C$ regions enable the formation of dimers.

The antigen specificity of an immunoglobulin molecule is conferred by the amino acid sequence of a variable, or V, region. As such, V regions of different immunoglobulin molecules can vary significantly depending upon their antigen specificity. Certain portions of a V region are invariant and are referred to as framework regions (FW regions). In contrast, certain portions of a V region are highly variable and are designated hypervariable regions. When the $V_L$ and $V_H$ domains pair in an immunoglobulin molecule, the hypervariable regions from each domain associate and create hypervariable loops that form antigen binding sites. Thus, the hypervariable loops determine the specificity of an immunoglobulin and are termed complementarity-determining regions (CDRs) because their surfaces are complementary to antigens.

Further variability of V regions is conferred by combinatorial variability of gene segments that encode an immunoglobulin V region. Immunoglobulin genes comprise multiple germline gene segments which somatically rearrange to form a rearranged immunoglobulin gene that encodes an immunoglobulin molecule. $V_L$ regions are encoded by a L chain V gene segment and J gene segment (joining segment). $V_H$ regions are encoded by a H chain V gene segment, D gene segment (diversity segment) and J gene segment (joining segment).

Both a L chain and H chain V gene segment contains three regions of substantial amino acid sequence variability. Such regions are referred to as L chain CDR1, CDR2 and CDR3, and H chain CDR1, CDR2 and CDR3, respectively. The length of an L chain CDR1 can vary substantially between different $V_L$ regions. For example, the length of CDR1 can vary from about 7 amino acids to about 17 amino acids. In contrast, the lengths of L chain CDR2 and CDR3 typically do not vary between different $V_L$ regions. The length of a H chain CDR3 can vary substantially between different $V_H$ regions. For example, the length of CDR3 can vary from about 1 amino acid to about 20 amino acids. In contrast, the lengths of H chain CDR1 and CDR2 typically do not vary between different $V_H$ regions. Each H and L chain CDR region is flanked by FW regions.

Another portion of an immunoglobulin molecule important in the targeting aspect of the present invention is the spacer or transmembrane spanning region.

Other functional aspects of an immunoglobulin molecule include the valency of an immunoglobulin molecule, the affinity of an immunoglobulin molecule, and the avidity of an immunoglobulin molecule. As used herein, affinity refers to the strength with which an immunoglobulin molecule binds to an antigen at a single site on an immunoglobulin molecule (i.e., a monovalent Fab fragment binding to a monovalent antigen). Affinity differs from avidity which refers to the sum total of the strength with which an immunoglobulin binds to an antigen. Immunoglobulin binding affinity can be measured using techniques standard in the art, such as competitive binding techniques, equilibrium dialysis or BlAcore methods. As used herein, valency refers to the number of different molecules an immunoglobulin molecule can combine with at one time. For example, a monovalent immunoglobulin molecule can only bind to one antigen at one time, whereas a bivalent immunoglobulin molecule can bind to two or more antigens at one time, and so forth.

In one embodiment of the present invention, a regulatory compound is a monovalent antibody. Such an antibody is not capable of aggregating receptors, which, without being bound by theory, is believed to enhance the ability of such an antibody to desensitize receptors expressed by a cell. Divalent antibodies can also be used in the present invention. Examples of divalent antibodies suitable as regulatory compounds of the present invention are described in detail in Example 9.

In one embodiment, the antibody is a bi-specific antibody, such as chimeric antibody. A bi-specific antibody is capable of binding two or more antigens, as with a divalent antibody, but in this case, the antigens are different antigens (i.e., the antibody exhibits dual specificity). A bi-specific antibody suitable for use in the present method includes an antibody having: (a) a first portion (e.g., a first antigen binding portion) which binds to the receptor and: (1) causes a dissociation of the extracellular ligand binding component from the transducer component when the components are associated with each other prior to contact with the compound; or (2) inhibits association of the extracellular ligand binding component with the transducer component when the components are dissociated from each other prior to contact with the compound; and (b) a second portion which binds to a cell surface molecule expressed by a cell which expresses the receptor. In this embodiment, the second portion can bind to any cell surface molecule, including to the receptor to be desensitized (i.e., the second portion of the bi-specific antibody binds to a different region of the receptor than the first portion of the bi-specific antibody). In a preferred embodiment, the second portion is capable of targeting the regulatory antibody to a specific receptor (i.e., the regulatory antibody binds to a target receptor, because it specifically recognizes that receptor, and it does not bind to other, different receptors). For example, the second portion of the bi-specific antibody can be an anti-idiotype antibody such that it binds to the antigen-binding region of a B cell antigen receptor. In the case of an Fc receptor, the second portion of the bi-specific antibody can be an antibody that specifically (i.e., selectively) recognizes a particular Fc receptor type (e.g., FcεRI), and therefore does not substantially bind to other Fc receptor types (e.g., FcγR, FcαR). Preferably, however, such antibodies do not substantially stimulate the receptor.

In one embodiment, the second portion binds to a cell surface molecule which is expressed by an autoreactive B cell. Such a cell surface molecule preferably distinguishes the autoreactive B cell from other B cells. In another embodiment, the second portion binds to a cell surface molecule which is expressed by a B cell involved in graft rejection.

Isolated antibodies of the present invention can include serum containing such antibodies, or antibodies that have been purified to varying degrees. Antibodies of the present invention can be polyclonal or monoclonal, functional equivalents such as antibody fragments (e.g., Fab fragments or $Fab_2$ fragments) and genetically-engineered antibodies, including single chain antibodies or chimeric antibodies that can bind to more than one epitope (i.e., bi-specific antibodies).

Generally, in the production of an antibody, a suitable experimental animal, such as a rabbit, hamster, guinea pig or mouse, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies. Such serum is useful as a reagent. Polyclonal antibodies can be further purified from the serum by, for example, treating the serum with ammonium sulfate. In order to obtain monoclonal antibodies, the immunized animal is sacrificed and B lymphocytes are recovered from the spleen. The differentiating and proliferating daughter cells of the B lymphocytes are then fused with myeloma cells to obtain a population of hybridoma cells capable of continual growth in suitable culture medium. Hybridomas producing a desired antibody are selected by testing the ability of an antibody produced by a hybridoma to bind to the antigen.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly. Antibodies raised against defined proteins or mimetopes can be advantageous because such antibodies are not substantially contaminated with antibodies against other substances that might otherwise cause interference in a diagnostic assay or side effects if used in a therapeutic composition. As used herein, the term "selectively binds to" refers to the ability of antibodies of the present invention to preferentially bind to specified proteins and mimetopes thereof. Binding can be measured using a variety of methods standard in the art including enzyme immunoassays (e.g., ELISA), immunoblot assays, etc.

As used herein, an isolated protein according to the present invention can be a full-length protein or any homologue of such a protein, such as a protein in which amino acids have been deleted (e.g., a truncated version of the protein, such as a peptide), inserted, inverted, substituted and/or derivatized (e.g., by glycosylation, phosphorylation, acetylation, myristoylation, prenylation, palmitation, amidation and/or addition of glycosylphosphatidyl inositol). A homologue of a protein is a protein having an amino acid sequence that is sufficiently similar to the natural protein amino acid sequence that a nucleic acid sequence encoding the homologue is capable of hybridizing under stringent conditions to (i.e., with) a nucleic acid molecule encoding the natural protein (i.e., to the complement of the nucleic acid strand encoding the natural protein amino acid sequence).

As used herein, a mimetope or mimic of a protein or antibody according to the present invention refers to any compound that is able to mimic the activity of a given protein or antibody, often because the mimetope has a structure that mimics the protein or antibody. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins or antibodies. Mimetopes can also be obtained by generating random samples of molecules, such as oligonucleotides, peptides or other organic or inorganic molecules, and. screening such samples by affinity chromatography techniques using the corresponding binding partner.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified. An isolated nucleic acid molecule of the present invention can be isolated from its natural source or produced using recombinant DNA technology (e.g., polymerase chain reaction (PCR) amplification, cloning) or chemical synthesis. Isolated nucleic acid molecules can include, for example, natural allelic variants and nucleic acid molecules modified by nucleotide insertions, deletions, substitutions, and/or inversions in a manner such that the modifications do not substantially interfere with the nucleic acid molecule's ability to encode a protein or to form stable hybrids under stringent conditions with natural gene isolates. An isolated nucleic acid molecule can include degeneracies. As used herein, nucleotide degeneracies refers to the phenomenon that one amino acid can be encoded by different nucleotide codons. Thus, the nucleic acid sequence of a nucleic acid molecule that encodes a protein can vary due to degeneracies.

A nucleic acid molecule homologue can be produced using a number of methods known to those skilled in the art (see, for example, Sambrook et al.). For example, nucleic acid molecules can be modified using a variety of techniques including, but not limited to, by classic mutagenesis and recombinant DNA techniques (e.g., site-directed mutagenesis, chemical treatment, restriction enzyme cleavage, ligation of nucleic acid fragments and/or PCR amplification), or synthesis of oligonucleotide mixtures and ligation of mixture groups to "build" a mixture of nucleic acid molecules and combinations thereof. Nucleic acid molecule homologues can be selected by hybridization with a naturally occurring gene or by screening the function of a protein encoded by a nucleic acid molecule.

As used herein, stringent hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31–9.62, 11.7 and 11.45–11.61). In addition, formulae to calculate the appropriate hybridization and wash conditions to achieve hybridization permitting varying degrees of mismatch of nucleotides are disclosed, for example, in Meinkoth et al., 1984, Anal. Biochem. 138, 267–284; Meinkoth et al., ibid., is incorporated by reference herein in its entirety.

More particularly, stringent hybridization conditions, as referred to herein, refer to conditions which permit isolation of nucleic acid molecules having at least about 70% nucleic acid sequence identity with the nucleic acid molecule being used to probe in the hybridization reaction, more particularly at least about 75%, and most particularly at least about 80%. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 0.1×SSC (0.157 M Na$^+$) at a temperature of between about 20° C. and about 35° C., more preferably, between about 28° C. and about 40° C., and even more preferably, between about 35° C. and about 45° C. In particular embodiments, stringent hybridization conditions for DNA:RNA hybrids include hybridization at an ionic strength of 0.1×SSC (0.157 M Na$^+$) at a temperature of between about 30° C. and about 45 ° C., more preferably, between about 38° C. and about 50° C., and even more preferably, between about 45° C. and about 55° C. These values are based on calculations of a melting temperature for molecules larger than about 100 nucleotides, 0% formamide and a G+C content of about 50%. Alternatively, $T_m$ can be calculated empirically as set forth in Sambrook et al., supra, pages 11.55 to 11.57.

As used herein, reference to a percent (%) identity refers to a BLAST homology search with the default parameters identified by the manufacturer.

Regulatory and therapeutic compounds of the present invention, including antibodies, proteins, peptides and mimetopes thereof, can be designed using structure based drug design. Structure based drug design refers to the use of computer simulation to predict a conformation of a peptide, polypeptide, protein, or conformational interaction between a peptide or polypeptide, and a therapeutic compound. For example, generally, for a protein to effectively interact with a therapeutic compound, it is necessary that the three dimensional structure of the therapeutic compound assume a compatible conformation that allows the compound to bind to the protein in such a manner that a desired result is obtained upon binding. According to the present invention, the step of designing can include creating a new chemical compound or searching databases of libraries of known compounds (e.g., a compound listed in a computational screening database containing three dimensional structures of known compounds). Designing can also be performed by simulating chemical compounds having substitute moieties at certain structural features. The step of designing can include selecting a chemical compound based on a known function of the compound. A preferred step of designing comprises computational screening of one or more databases of compounds in which the three dimensional structure of the compound is known and is interacted (e.g., docked, aligned, matched, interfaced) with the three dimensional structure of a receptor of the present invention by computer (e.g. as described by Humblet and Dunbar, *Animal Reports in Medicinal Chemistry*, vol. 28, pp. 275–283, 1993, M Venuti, ed., Academic Press). Methods to synthesize suitable chemical compounds are known to those of skill in the art and depend upon the structure of the chemical being synthesized. Methods to evaluate the bioactivity of the synthesized compound depend upon the bioactivity of the compound (e.g., inhibitory or stimulatory) and are disclosed herein.

Various other methods of structure-based drug design are disclosed in Maulik et al., 1997, Molecular Biotechnology. *Therapeutic Applications and Strategies*, Wiley-Liss, Inc., which is incorporated herein by reference in its entirety. Maulik et al. disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

As discussed above, in one embodiment of the present invention, the receptor is selected from the group of a B cell antigen receptor, a pro-B cell receptor, and a pre-B cell receptor. In this embodiment, the transducer component is selected from the group of Igα and Igβ. In one aspect of the invention, the regulatory compound selectively binds to the transducer component and prevents or inhibits association of the extracellular ligand binding component with the transducer component. In one embodiment, the extracellular binding component comprises an mIg selected from the group consisting of mIgD and mIgM, although the extracellular ligand binding component can be different, for example, when the B cell expressing the receptor is a pro-B cell or a pre-B cell. In one embodiment, the B cell antigen receptor selectively binds to an antigen associated with an autoimmune disease; in another embodiment, the B cell antigen receptor selectively binds to an antigen associated with a graft cell. B cells which express receptors that are suitable for desensitizing according to the present invention include, but are not limited to, an autoreactive B cell, a B cell comprising a B cell antigen receptor that selectively binds to an antigen on a graft, a B cell lymphoma and a chronic lymphocytic leukemia cell. B cells that are suitable for sensitizing according to the present invention include any normal B cell. In one embodiment of the present invention, the regulatory compound is contacted with the B cell receptor by administering the regulatory compound to a patient that has an autoimmune disease selected from the group of rheumatoid arthritis, systemic lupus erythematosus, insulin dependent diabetes mellitis, multiple sclerosis, myasthenia gravis, Grave's disease, autoimmune hemolytic anemia, autoimmune thrombocytopenia purpura, Goodpasture's syndrome, pemphigus vulgaris, acute rheumatic fever, post-streptococcal glomerulonephritis, or polyarteritis nodosa.

In another embodiment of the present invention, the receptor to be targeted by the method of the present invention is a human Ig Fc receptor selected from the group consisting of FcαRl, FCεRI, FcγRI, FcγRIIa, FcγRIIb, FcγRIIc, FcγIIIb. In this embodiment, the regulatory compound selectively binds to an extracellular ligand binding domain of the Fc receptor. Typically, the extracellular binding component comprises an a receptor. In one embodiment, the receptor is an FcεRI receptor comprising an a receptor extracellular ligand binding component and a β/γ transducer component. In another embodiment, the receptor is expressed by a cell selected from the group consisting of a mast cell and a basophil. In one embodiment, the regulatory compound is contacted with the receptor by administration of the regulatory compound to a patient that has a condition associated with inflammation. In one embodiment, the condition is associated with allergic inflammation. Various inflammatory conditions suitable for treatment using the method of the present invention are discussed below.

The method of the present invention includes a step of contacting the regulatory compound with the receptor to be desensitized. According to the present invention, the step of contacting can be conducted in vivo, in vitro and/or ex vivo. When the step of contacting is conducted in vitro, such as in an assay, the step of contacting can include contacting the compound and receptor such as by mixing or combining the compound and receptor in culture. When the method is used in an assay, the receptor can be free receptor or a expressed by a cell (i.e., a cell based assay). As used herein, in vivo delivery refers to the administration of a regulatory compound directly to a subject. Suitable methods of administration are discussed below. Ex vivo delivery of a regulatory compound refers to a method that includes the steps of contacting a population of cells removed from an subject with a regulatory compound of the present invention under conditions such that the regulatory compound interacts with targeted cell types (i.e., T cells) and returning the contacted cells to the subject. Methods to achieve such interaction include, but are not limited to, transfection, retroviral infection, electroporation, lipofection, bacterial transfer, spheroplast fusion, and adsorption.

Acceptable protocols to administer compositions in an effective manner include individual dose size, number of doses, frequency of dose administration, and mode of administration. Determination of such protocols can be accomplished by those skilled in the art. A suitable single dose is a dose that is capable of desensitizing at least about 10% of the target receptors on at least one cell, and in increasing order of preference, more preferably about 20%, about 30%, about 40%, about 50%, about 60%, about 70%, about 80%, about 90% and most preferably, about 100%, of the target receptors on at least one cell when administered one or more times over a suitable time period. For example, a preferred single dose of a regulatory compound can range from about 1 ng (nanogram) to 1 microgram ($\mu$g, also denoted $\mu$g) to about 10 milligrams (mg) of the composition per kilogram body weight of the animal. Additional doses preferably are administered when the response of the animal becomes insufficient to achieve the desired desensitization effect.

The manner of administration of a regulatory compound and/or therapeutic composition of the present invention can depend upon the particular purpose for the delivery (e.g., treatment of disease, use as a diagnostic reagent), the overall health and condition of the recipient and the judgement of the physician or technician administering the target vehicle. A therapeutic composition of the present invention can be administered to an animal using a variety of methods. Such delivery methods can include parenteral, topical, oral or local administration, such as intradermally or by aerosol. A therapeutic reagent can be administered in a variety of unit dosage forms depending upon the method of administration. For example, unit dosage forms suitable for oral administration to the intestinal region of an animal include powder, tablets, pills and capsules. Preferred delivery methods for a therapeutic composition of the present invention include intravenous administration, local administration by, for example, injection, intradermal injection, intramuscular injection and inhalation. For particular modes of delivery, a therapeutic composition of the present invention can be formulated in a carrier or an excipient of the present invention.

As used herein, a pharmaceutically acceptable carrier refers to any substance suitable as a vehicle for delivering an compound or therapeutic composition to a suitable in vitro or in vivo site of action. As such, carriers can act as an excipient for formulation of a therapeutic or experimental reagent. Preferred carriers are capable of maintaining the compound or therapeutic composition in a form that is capable of interacting with a receptor according to the present invention. Examples of such carriers include, but are not limited to, water, phosphate buffered saline, saline, Ringer's solution, dextrose solution, serum-containing solutions, Hank's solution and other aqueous physiologically balanced solutions. Aqueous carriers can also contain suitable auxiliary substances required to approximate the physiological conditions of the recipient, for example, enhancement of chemical stability and isotonicity. Suitable auxiliary substances include, for example, sodium acetate, sodium chloride, sodium lactate, potassium chloride, calcium chloride, sorbitan monolaurate, triethanolamine oleate, and other substances used to produce phosphate buffer, Tris buffer, and bicarbonate buffer. Auxiliary substances can also include preservatives, such as thimerosal, m or o-cresol, formalin and benzyl alcohol. Preferred auxiliary substances for aerosol delivery include surfactant substances nontoxic to a recipient, for example, esters or partial esters of fatty acids containing from about 6 to about 22 carbon atoms. Examples of esters include, caproic, octanoic, lauric, palmitic, stearic, linoleic, linolenic, olesteric, and oleic acids. Reagents of the present invention can be sterilized by conventional methods and/or lyophilized. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration. Carriers also include compounds that increase the half-life of a therapeutic composition in the treated animal. Such suitable carriers include, but are not limited to, polymeric controlled release vehicles, biodegradable implants, liposomes, bacteria, viruses, other cells, oils, esters, and glycols.

According to the present invention, the method of desensitizing a receptor can be used to treat a condition associated with inflammation, such as allergic inflammation. Allergic inflammation is a condition in which the elicitation of one type of immune response (e.g., a Th2-type immune response) against a sensitizing agent, such as an allergen, can result in the release of inflammatory mediators that recruit cells involved in inflammation in a mammal, the presence of which can lead to tissue damage and sometimes death. Preferred diseases associated with allergic inflammation which are preferable to treat using the method and composition of the present invention include, allergic airway diseases, allergic rhinitis, allergic conjunctivitis and food allergy. Other conditions which are associated with inflammation, are well known in the art and include, but are not limited to, autoimmune diseases and infectious diseases.

An autoimmune disease to treat can be any autoimmune disease, including, but not limited to, rheumatoid arthritis, systemic lupus erythematosus, insulin dependent diabetes mellitis, multiple sclerosis, myasthenia gravis, Grave's disease, autoimmune hemolytic anemia, autoimmune thrombocytopenia purpura, Goodpasture's syndrome, pemphigus vulgaris, acute rheumatic fever, post-streptococcal glomerulonephritis, and polyarteritis nodosa. Preferred BCR autoantigen specificities to target include, but are not limited to, at least a portion of a thyroid-stimulating hormone receptor, pancreatic β cell antigens, epidermal cadherin, acetyl choline receptor, platelet antigens, nucleic acids, nucleic acid:protein complexes, myelin protein, thyroid antigens, joint antigens, antigens of the nervous system, salivary gland proteins, skin antigens, kidney antigens, heart antigens, lung antigens, eye antigens, erythrocyte antigens, liver antigens and stomach antigens.

The methods of the present invention can be used to treat any animal, and preferably, those of the mammalian class Mammalia, and more preferably, include domestic animals, commercially valuable animals, laboratory animals and humans.

One embodiment of the present invention relates to an isolated regulatory compound that desensitizes a receptor selected from the group consisting of a B cell antigen receptor and an Ig Fc receptor, wherein the receptor has an extracellular ligand binding component and a transducer component, the regulatory compound being identified by its ability to selectively bind to the receptor and upon the binding, is capable of: (1) inducing the extracellular ligand binding component to dissociate from the transducer component; and/or (2) inhibiting the extracellular ligand binding component from associating with said transducer component. Another embodiment of the present invention relates to an isolated regulatory compound that enhances or prolongs sensitization of a receptor selected from the group of BCR, pro-BCR, pre-BCR, FcR and NK receptor. Such a compound is identified as being capable of: (1) causing the extracellular ligand binding component to associate with the transducer component when the two components are not associated with each other prior to contact by the compound; or (2) prolonging or enhancing the time over which the extracellular ligand binding component is associated with the transducer component when the components are associated prior to contact by the compound, thereby sensitizing the receptor. Various aspects of such regulatory compounds have been described in detail above.

One embodiment of the present invention relates to a method for sensitizing or enhancing sensitization of a receptor selected from the group of BCR, pro-BCR, pre-BCR, FcR and NK receptor. Such a method includes the step of contacting a compound with a receptor that has an extracellular ligand binding component and a transducer component, wherein the compound: (1) causes the extracellular ligand binding component to associate with the transducer component when the two components are not associated with each other prior to contact by the compound; or (2) prolongs or enhances the time over which the extracellular ligand binding component is associated with the transducer component when the components are associated prior to contact by the compound, thereby sensitizing the receptor. Such a method is particularly useful when a receptor has become refractory to sensitization, and sensitization is desired, or when an enhanced receptor response is desired (i.e., the method increases sensitization of the receptor, typically by prolonging sensitization). For example, prolonged or enhanced immune response are desirable in vaccination protocols or treatments against particular diseases, such as cancer or HIV infection. In general, the methods described herein with regard to receptor desensitization, can be applied appropriately to receptor sensitization and to methods of identifying regulatory compounds that enhance or prolong sensitization of receptors. In one embodiment of this method, an additional factor can be contacted with the B cell antigen receptor, such as an antigen or other factor which enhances vaccination against a given antigen or enhancement of the B cell antigen response.

Another embodiment of the present invention relates to a method to identify compounds useful for desensitizing a receptor. One such method includes the steps of: (a) contacting with a putative regulatory compound a receptor selected from the group of a B cell antigen receptor, a pro-B cell receptor, a pre-B cell receptor, an Fc receptor, and an NK receptor, wherein the receptor comprises an extracellular ligand binding component and at least one transducer component, and wherein the extracellular ligand binding component is associated with the transducer component prior to contact of the receptor with the putative regulatory compound; and, (b) detecting whether the putative regulatory compound, when contacted with the receptor, causes the extracellular ligand binding component to dissociate from the transducer component. A putative regulatory compound that causes the dissociation is identified as a regulatory compound.

Another such method includes the steps of: (a) contacting with a putative regulatory compound, a receptor selected from the group of a B cell antigen receptor, an Fc receptor, and an NK receptor, wherein the receptor includes an extracellular ligand binding component and at least one transducer component, and wherein the extracellular ligand binding component is not associated with the transducer component prior to contact with the putative regulatory compound; and, (b) detecting whether the putative regulatory compound, when contacted with the receptor, inhibits the extracellular ligand binding component from associating with the transducer component. A putative regulatory compound that inhibits the association is identified as a regulatory compound. As used herein, the term "putative" refers to compounds having an unknown regulatory activity, at least with respect to the ability of such compounds to desensitize receptors as described herein.

In both embodiments of the method of identifying a regulatory compound according to the present invention, the method can be a cell-based assay, or non-cell-based assay. In a preferred embodiment, the receptor is expressed by a cell (i.e., a cell-based assay). In accordance with the present invention, such a method is conducted under conditions which are effective to screen for regulatory compounds useful in the method of the present invention. Effective conditions include, but are not limited to, appropriate media, temperature, pH and oxygen conditions that permit cell growth. An appropriate, or effective, medium refers to any medium in which a cell of the present invention, when cultured, is capable of cell growth and expression of BCR, FcR or NK receptor. Such a medium is typically a solid or liquid medium comprising growth factors and assimilable carbon, nitrogen and phosphate sources, as well as appropriate salts, minerals, metals and other nutrients, such as vitamins. Culturing is carried out at a temperature, pH and oxygen content appropriate for the cell. Such culturing conditions are within the expertise of one of ordinary skill in the art.

In the first embodiment, the conditions under which a receptor according to the present invention is contacted with a putative regulatory compound, such as by mixing, are conditions in which the receptor components are associated if essentially no regulatory compound is present. For example, such conditions include normal culture conditions in the absence of a stimulatory compound, such as the natural ligand for the receptor, an anti-idiotype antibody, or other equivalent stimulus. In this embodiment, when the assay is a cell-based assay, the putative regulatory compound is then contacted with the receptor. Without being bound by theory, given the experimental data provided herein, the present inventors believe that receptor complexes may normally exist in an equilibrium between stable and unstable configurations. Therefore, in the absence of an appropriate stimulator, such as the receptor's natural ligand, an anti-idiotype antibody, or an equivalent stimulus, both associated and dissociated receptors are likely to be present on the cell surface. Therefore, the step of detecting in such an assay is designed to indicate whether a physical association between components can be disrupted by the putative regulatory compound.

In the second embodiment, the conditions under which a receptor according to the present invention is contacted with a putative regulatory compound, such as by mixing, are conditions in which the receptor components are not normally associated if essentially no regulatory compound is present. Such conditions can include, for example, contact of said receptor with a stimulator molecule which causes the receptor components to dissociate. Alternatively, as discussed above, such conditions include normal culture conditions in the absence of a stimulus, since the present inventors believe that complexes may normally exist in an equilibrium between stable and unstable configurations. Preferably, however, such conditions include contacting the receptor with its natural ligand or an equivalent stimulus, such that the components are induced to dissociate.

The assay of the present invention can also be a non-cell based assay. In this embodiment, the putative regulatory compound can be directly contacted with an isolated receptor, or a receptor component (i.e., an isolated transducer component or an isolated extracellular ligand binding component), and the ability of the putative regulatory compound to bind to the receptor or receptor component can be evaluated, such as by an immunoassay or other binding assay. The assay can then include the step of further analyzing whether putative regulatory compounds which bind to a portion of the receptor (e.g., a portion of a transducer component or extracellular ligand binding component), is capable of inhibiting association of the receptor components or is capable of causing dissociation of the receptor components. Such further steps can be performed by cell-based assay, as described above, or by non-cell-based assay.

In either embodiment of the present invention, the step of detecting includes any method that measures: (1) the ability of a receptor to transduce a signal as a result of stimulation of the receptor, wherein a reduced ability of the receptor to transduce a signal as a result of stimulation when contacted with the putative regulatory compound, as compared to in the absence of contact with the compound, indicates that the compound desensitizes the receptor; and/or (2) the physical association or dissociation state of the transducer and extracellular ligand binding component. Such assays include bioassays and molecular assays, including, but not limited to, calcium mobilization assays, phosphorylation assays, kinase assays, immunofluorescence microscopy, flow cytometry, immunoprecipitation assays, immunoblots, enzyme-linked immunosorbant assays, radioimmunoassays, and other binding assays, biological assays and/or combinations thereof. Several of such assays are described in the Examples section.

By performing additional fine specificity analysis of where identified regulatory compounds of the present invention contact the receptor components and/or precisely how such components are causing receptor destabilization, such as for the antibodies described in Example 9, the target sequence of the receptor components (i.e., the sequence of the portion of the receptor which, if blocked, bound, altered or otherwise disrupted, causes receptor dissociation/destabilization or inhibits association) can be identified and used in rational drug design, for example.

The following examples are provided for the purposes of illustration and are not intended to limit the scope of the present invention.

EXAMPLES

Materials and Methods Used in the Following Examples

Cell isolation and stimulation: The K46$\mu$ lymphoma cells, expressing mIgM specific for NP, were cultured as previously described (Hombach et al., 1990; Kim et al., 1979; Reth et al., 1987; Vilen et al., 1997). Cells were stimulated with doses of NP$_7$BSA ranging from 25–500mg/5×10$^6$/ml for 1–2 hours at 37° C. Under conditions of desensitization (25ng/5×10$^6$/ml=25% receptor occupancy), the majority of receptors remained available to bind the challenge dose of antigen (2 $\mu$g/5×10$^6$/0.1 ml NP$_7$BSA) as previously characterized (Vilen et al., 1997). Alternatively, cells were stimulated with biotinylated anti-$\mu$ (b-7-6) at 10 $\mu$g/5×10$^6$/ml. To avidin immunoprecipitate unstimulated cells (FIG. 1 lane 7), biotinylated b-7-6 was bound for 2 minutes at 4° C. prior to cell lysis. For surface biotinylation experiments, cells were either stimulated at 37° C. for 1 hour or at room temperature for 15 minutes followed by 4° C. for 45 minutes to slow cell surface receptor loss.

Resting ($\rho$>1.066 or 1.070) B lymphocytes were isolated from spleens of 3–83 $\mu\delta$Ig transgenic mice (on B10.D2 background) as previously described (Cambier et al., 1988; Russell et al., 1991). These transgenic mice contain normal levels of splenic B lymphocytes compared to non-transgenic B10.D2 mice. Resting 3–83 B cells express both IgM and IgD receptors specific for H-2K$^k$ and respond to receptor crosslinking by Ca$^{2+}$ mobilization and tyrosyl phosphorylation comparably to B10.D2-derived B cells. Stimulation of the 3–83 $\mu\delta$ B lymphocytes using an antigen mimetic peptide-dextran conjugate (3–83ag1$_{50}$Dex) at a dose of 2 $\mu$g/5×10$^6$ ml (Vilen et al., 1997). The Ag-mimetic sequence, CAHDWRSGFGGFQHLCCGAAGA (SEQ ID NO: 1) was defined by screening a phage display library using the 3–83 immunoglobulin (Sparks et al., 1995). The binding of the mimetic peptide to the 3–83 immunoglobulin was shown to be specific for the antigen combining site based on an ELISA assay using isotype matched immunoglobulin. In addition, an anti-idiotypic antibody specific for the 3–83 receptor (54.1) competed for peptide binding (Carbone and Cambier, unpublished data).

Pervanadate Stimulation and Herbimycin treatment. Cells were stimulated for 10 minutes at a final concentration of 30$\mu$M sodium orthovanadate using freshly prepared solution of 10 mM sodium orthovanadate/30 mM hydrogen peroxide. Alternately, cells (2×10$^6$ cells/ml) were treated with 5 $\mu$M herbimycin (Calbiochem, LaJolla, Calif.) for 16 hours prior to desensitization.

Antibodies and Immunoprecipitation. The monoclonal antibodies b-7-6 (anti-$\mu$), HM79 (anti-Ig-$\beta$) and L22.12.4 (anti-$\lambda$) were purified from culture supernatants (Koyama et al., 1997). The HB-$\delta$6 (anti-$\delta$) used for immunoprecipitation and the polyclonal goat anti-mouse IgD for immunoblotting were provided by Fred Finkleman. The rabbit polyclonal anti-Ig-$\alpha$ and anti-Ig-$\beta$ were prepared against the cytoplasmic tails of the molecules (residues 160–220 of mouse Ig-$\alpha$ and residues 181–246 of mouse Ig-$\beta$). The rabbit polyclonal anti-Lyn and anti-Syk have been previously described (Vilen et al., 1997). Other primary antibodies for Western blotting include: goat anti-mouse IgM-HRP (Southern Biotechnology Associates, Birmingham, Ala.), and the anti-phosphotyrosine antibody, Ab-2, (Oncogene Science, Manhasset, N.Y.). HRP-conjugated secondary antibodies include: rat anti-mouse IgG$_1$ (Biosource Intl. Camarillo, Calif.), protein A (Zymed, S. San Francisco, Calif.), rabbit anti-goat Ig (Sigma, St. Louis, Mo.) and streptavidin (Pierce, Rockford, Ill.).

Cell lysates from 15–25×10$^6$ cells were prepared in buffer containing 0.33% CHAPS, 150 mM NaCl, 10 mM Tris (pH 7.5), 2mM sodium o-vanadate, 1 mM PMSF, 0.4 mM EDTA, 10 mM NaF, and 1 $\mu$g/ml each of aprotinin, leupeptin and $\alpha$1-antitrypsin. Lysates were held on ice 10 minutes and then particulate material removed by centrifugation at 12,000×g for 10 minutes. Antibodies used in immunoprecipitations were conjugated to CNBr-activated Sepharose 4B according to manufacturers instruction (Pharmacia Biotech, Uppsala, Sweden). The streptavidin immunoprecipitations were performed using streptavidin agarose (Pierce, Rockford, Ill.). Approximately 0.5–1$\mu$ of precipitating antibody was incubated with 1×10$^6$ cell equivalents of cleared lysate for 30 minutes at 4°. Immunoprecipitates were washed twice with lysis buffer, then fractionated using 10% SDS-PAGE gels. Fractionated proteins were transferred to polyvinylidene difluoride membranes using a semidry blotting apparatus following the conditions recommended by the manufacturer (Millipore Corp., Bedford, Mass.). Immunoreactive proteins were detected by enhanced chemiluminescence detection (ECL, NEN, Boston, Mass.).

Surface biotinylation. Cells were washed 3 times with PBS then resuspended at 10×10$^6$/ml in PBS containing 50 $\mu$g/ml sulfo-NHS-biotin (Pierce, Rockford, Ill.). After incubation for 10 minutes at room temperature, the cells were washed twice with cold PBS containing 15 mM glycine, then resuspended at 5×10$^6$/ml in IMDM containing 2% FCS, then stimulated as described above.

Surface staining. K46$\mu$ cells were untreated or treated with non-biotinylated NP$_7$BSA for 2 hours at 37° C. (25 ng/5×10$^6$ cells/ml) then stained at 4° C. in the presence 0.2% azide with biotinylated anti-Ig-$\beta$ (HM79) or biotinylated NP$_7$BSA to determine the presence of surface Ig-$\beta$ and antigen binding receptors respectively. The samples were washed extensively with cold staining medium (balanced salt solution containing 2% calf serum and 0.2% azide) followed by secondary staining with phycoerythrin-conjugated avidin for 20 minutes. Analysis was performed on FACScan (Becton Dickinson, Mountain View, Calif.).

EXAMPLE 1

The following example shows that Ig-$\alpha$ and Ig-$\beta$ signal transducing subunits of the BCR are destabilized from IgM following antigen stimulation.

Previous studies of desensitized cells suggested that the defect in BCR signaling lies upstream of src-family kinase activation, possibly at the level of the receptor (Vilen et al., 1997). To address changes in BCR structure under conditions of receptor desensitization, the $\mu$-heavy chain, Ig-$\alpha$ or Ig-$\beta$ were immunoprecipitated from desensitized K46$\mu$ cell lysates and the coprecipitated BCR components were quantitated. Briefly, a comparative analysis of mIg-Ig-$\alpha$/Ig-$\beta$ association in unstimulated K46$\mu$ cells, cells stimulated 1 hour with NP$_7$BSA (500 mg/5×10$^6$ cells/ml) or cells stimulated 1 hour with biotinylated b-7-6 (10 $\mu$g/5×10$^6$/ml) was performed. Biotinylated b-7-6 was prebound to unstimulated cells (10 $\mu$g/5×10$^6$ cells/ml) for 2 minutes at 4° C. prior to lysis. FIG. 1 shows the results of the analysis as follows: Panel 1: Lanes 1 and 2 represent IgM and Ig-$\alpha$ immunoblots of anti-$\mu$ immunoprecipitates. Panel 2: Lanes 3 and 4 represent IgM, Ig-$\beta$ and Ig-$\alpha$ immunoblots of anti-Ig-$\beta$ immunoprecipitates. Panel 3: Lanes 5 and 6 represent IgM and Ig-$\alpha$ immunoblots of Ig-$\alpha$ immunoprecipitates. Panel 4: Lanes 7 and 8 represent IgM and Ig-$\alpha$ immunoblots of streptavidin immunoprecipitates.

As shown in FIG. 1, panel 1, IgM ($\mu$-heavy chain) from cells stimulated 1 hour with antigen (desensitized) coprecipitated with approximately 67% less (determined by densitometry) Ig-$\alpha$ compared to IgM from unstimulated cells. Similarly, Ig-$\beta$ and Ig-$\alpha$ (FIG. 1, panel 2 and 3) from cells stimulated for 1 hour coprecipitated with 50–66% less IgM ($\mu$-heavy chain) than unstimulated cells. This loss of coprecipitable Ig-$\alpha$ was not simply due to movement of receptors to the cytoskeletal/detergent insoluble fractions, as the levels of IgM (panel 1) or Ig-$\alpha$/Ig-$\beta$-0 (panel 2 and 3) remained constant. The failure of the transfected IgM receptor in the K46$\mu$ cells to rapidly downmodulate was not due to a defect in cytoskeletal association as high affinity anti-receptor antibodies and prolonged incubation with antigen (>3 hours) caused receptor downmodulation (FIG. 1 panel 4 and data not shown). The above results show that within 1 hr of BCR aggregation by moderate affinity antigen (defined as K$_D$=1.5×10$^{-5}$ for NP binding B-1-8 (data not shown) and approximately 10$^{-5}$ to 10$^{-6}$ for H-2K$^b$ binding 3–83 (Lang et al., 1996)), significantly less Ig-$\alpha$/Ig-$\beta$ dimer is associated with mIgM, suggesting a dissociation or destabilization of the BCR complex in antigen desensitized cells.

EXAMPLE 2

The following example shows that the timing of BCR destabilization is coincident with receptor desensitization.

Figure 2A:
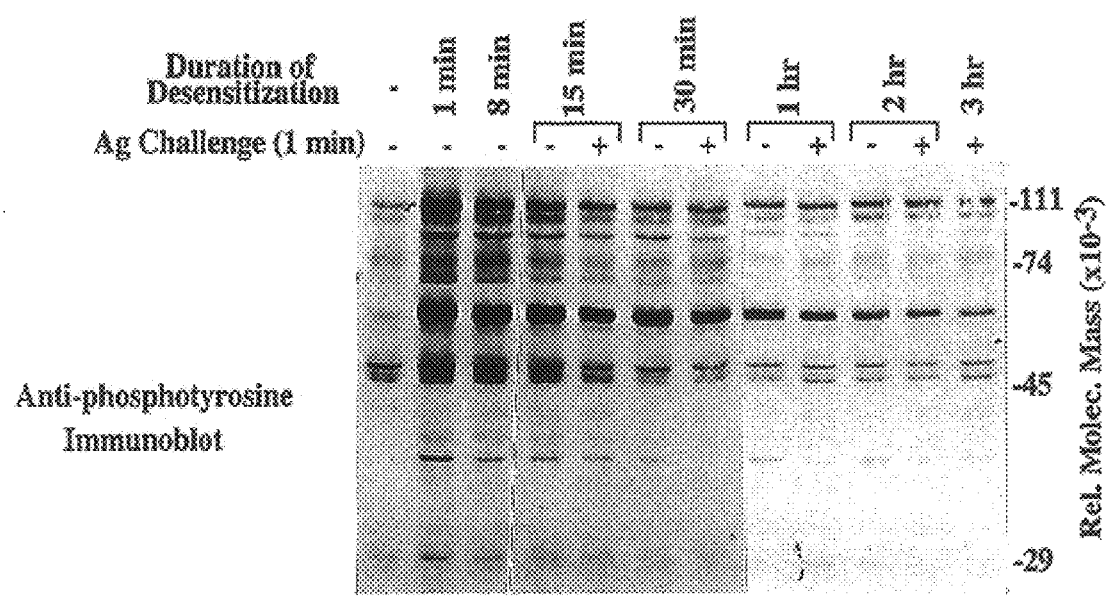
FIG. 2A is a digitized image of an anti-phosphotyrosine immunoblot of K46μ cells that were desensitized with a low dose of NP$_7$BSA.

To establish the temporal relationship between BCR destabilization and receptor desensitization, a time course analysis was performed to determine the time required to desensitize and destabilize the BCR. FIG. 2A is an anti-phosphotyrosine immunoblot of K46$\mu$ cells that were desensitized with a low dose of NP$_7$BSA (25 ng/5×10$^6$ cells/ml) for 15 minutes (lane S), 30 minutes (lane 7), 1 hour (lane 9), 2 hours (lane 11), and 3 hours (lane 12), then challenged with high dose NP$_7$BSA (2 $\mu$g/5×10$^6$ cells/0.1 ml) for 1 minute. Alternatively, control cells were stimulated with the desensitizing dose of NP$_7$BSA (25 ng/5×10$^6$ cells/ml) for 1 minute (lane 2), 8 minutes (lane 3), 15 minutes (lane 5), minutes (lane 6), 1 hour (lane 8), and 2 hours (lane 10) to establish the baseline tyrosine phosphorylation prior to challenge. As shown in FIG. 2A, at time points earlier than 30 minutes the tyrosine phosphorylation induced by the desensitizing antigen (25% receptor occupancy) had not decayed sufficiently to allow assessment of whether the receptors could respond to challenge (compare lane 4 to lane 2). However, by 30 minutes the basal tyrosine phosphorylation had declined significantly to see an antigen induced response, yet these cells failed to respond to subsequent receptor engagement (100% receptor occupancy) reflecting the desensitization of the BCR at this time point.

Figure 2B:
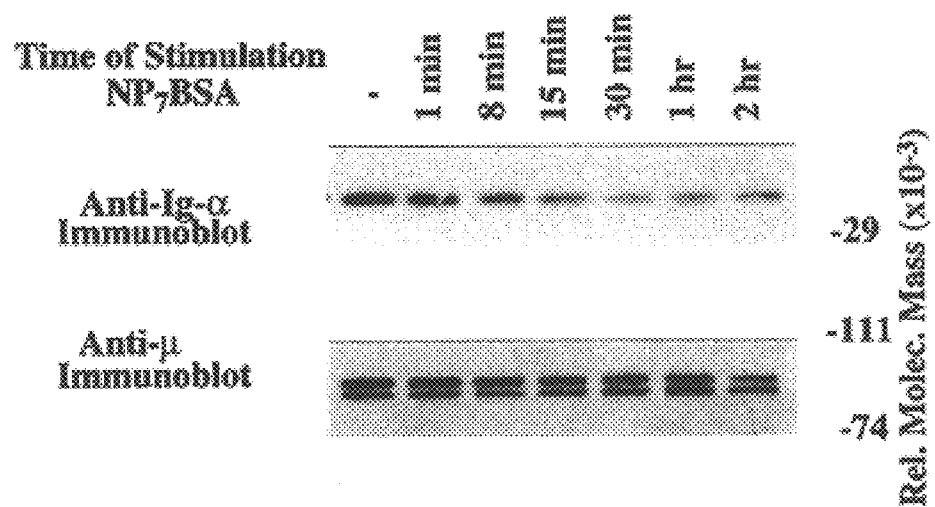
FIG. 2B is a digitized image of anti-Ig-α and anti-μ immunoblots of anti-μ immunoprecipitates from unstimulated K46μ cells and cells stimulated with NP$_7$BSA over a time course.

To determine the time required for destabilization of the BCR complex a time course analysis was again performed. FIG. 2B shows anti-Ig-α and anti-μ immunoblots of anti-μ immunoprecipitates from unstimulated K46μ cells (lane 1), cells stimulated 1 minute (lane 2), 8 minutes (lane 3), 15 minutes (lane 4), 30 minutes (lane 5), 1 hour (lane 6) and 2 hours (lane 7) with 500 mg/5×10$^6$ cells/ml NP$_7$BSA. As shown in the top panel of FIG. 2B, cells stimulated for 15 minutes exhibited a 50% loss of coprecipitable Ig-α and at 30 minutes an 80% diminution. This did not reflect loss of detergent soluble cell surface receptor as the level of precipitable IgM remained relatively constant over the duration of the time course (FIG. 2B, bottom panel).

Figure 2C:
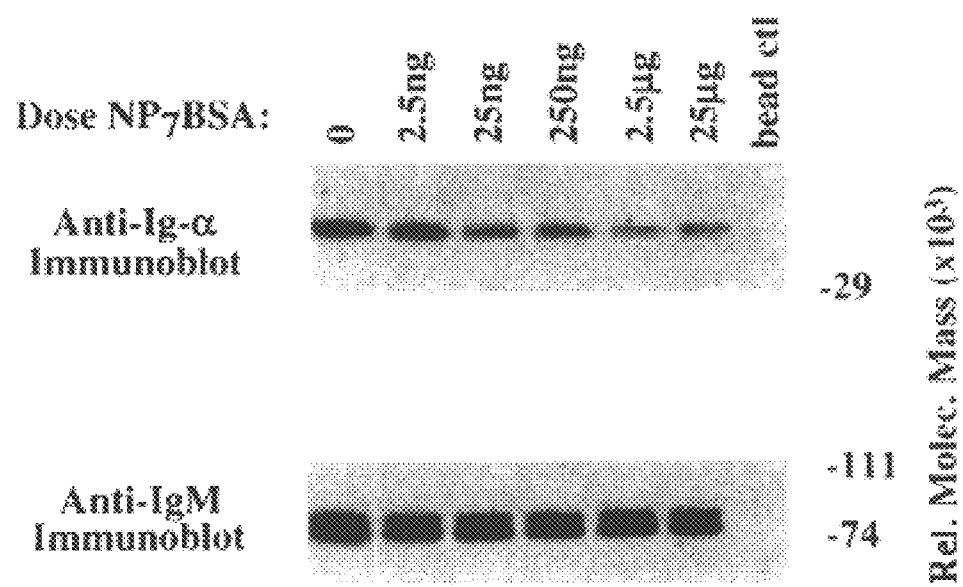
FIG. 2C is a digitized image of anti-Ig-α and anti-μ immunoblots of anti-μ immunoprecipitates from unstimulated K46μ cells and cells stimulated with increasing doses of NP$_7$BSA.

To determine if destabilization of the BCR occurred in a dose dependent fashion, cells were treated with increasing doses of NP$_7$BSA. FIG. 2C shows anti-Ig-α and anti-μ immunoblots of anti-μ immunoprecipitates from unstimulated K46μ cells (lane 1), cells stimulated 1 hour with 2.5 ng/5×10$^6$/ml (lane 2), 25 ng/5×10$^6$/ml (lane 3), 250 ng/5×10$^6$/ml (lane 4), 2.5 μg/5×10$^6$/ml (lane 5), 25 μg/5×10$^6$/ml (lane 6) or lysates immunoprecipitated with blocked agarose beads (lane 7). As shown in FIG. 2C, a non-desensitizing, non-signal inducing, antigen dose (2.5ng/5×10$^6$/ml) (Vilen et al., 1997) did not induce significant BCR destabilization. However, higher doses of antigen (25 ng–25 μg) induced similar levels of receptor destabilization. These data show that BCR destabilization is dose dependent, requiring only a low dose of antigen, and increasing antigen dose does not increase the level of receptor destablization. In addition, both the timing and dose requirements of BCR destabilization appear coincident with receptor desensitization.

EXAMPLE 3

The following example demonstrates that IgM and IgD-containing BCR are destabilized following antigen stimulation.

Figure 3:
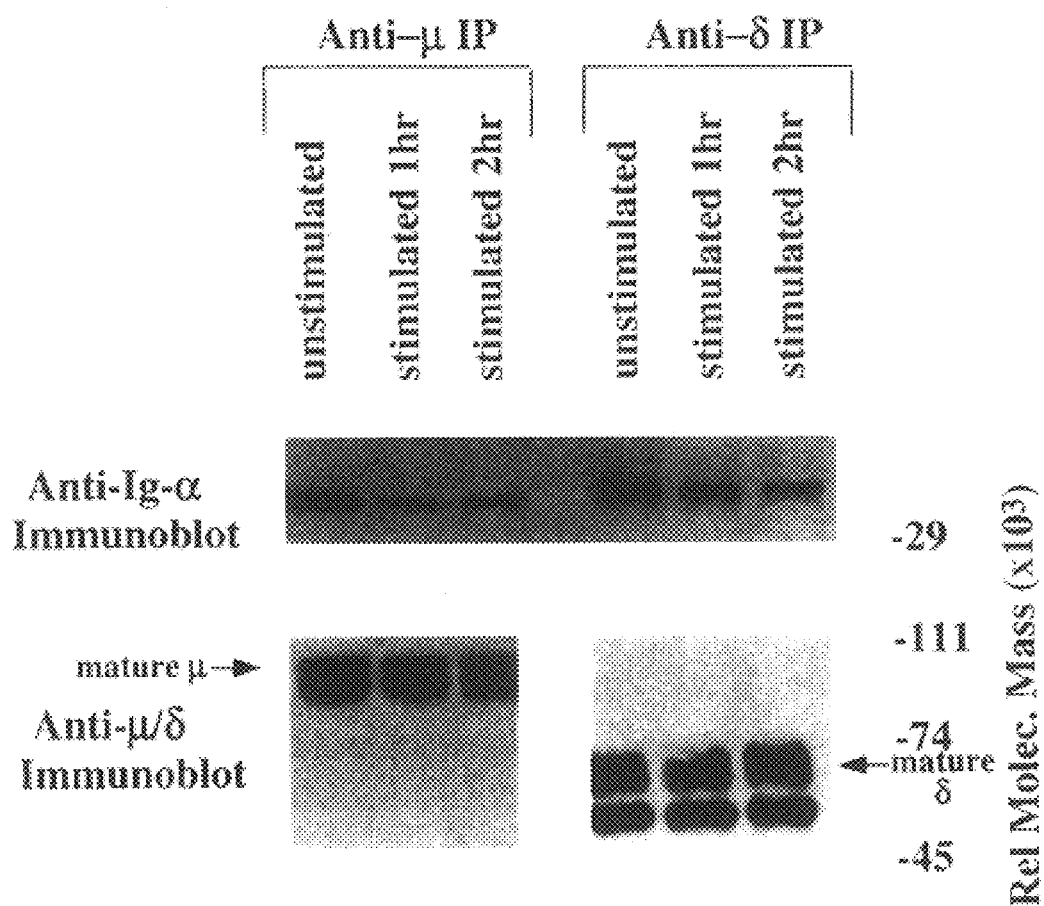
FIG. 3 is a digitized image showing that mIg-Ig-α/Ig-β destabilization occurs in both IgM and IgD containing receptors.

To address whether the destabilization of BCR occur in both in IgM and IgD-containing receptors, resting splenic B cells from 3–83 μδ transgenic mice were desensitized with antigen as previously described (Vilen et al., 1997). FIG. 3, showing anti-Ig-α or anti-δ immunoblots of antiμ or anti-δ immunoprecipitates, demonstrates that mIg-Ig-α/Ig-β destabilization occurs in both IgM and IgD containing receptors. IgM and IgD receptors from 3–83 μδ transgenic B cells were immunoprecipitated from unstimulated cells (lane 1 and lane 4), cells stimulated 1 hour with 2 μg/3–83 ag1$_{50}$Dex/5×10$^6$/ml (lane 2 and lane 5) or cells stimulated 2 hours with 2 μg/3–83ag1$_{50}$Dex/5×10$^6$/ml (lane 3 and lane 6). Serial immunoprecipitation with anti-μ then anti-δ, followed by Ig-δ immunoblotting revealed that BCR containing both isotypes were destabilized following exposure to antigen for 1 hr (FIG. 3 lane 2 and lane 5) or 2 hrs (lanes 3 and 6). Again this was not due to unequal immunoprecipitation of membrane immunoglobulin. These data demonstrate that antigen induces destabilization of the BCR complex in B lymphocytes and shows that both μ and δ-containing receptors are subject to this effect.

EXAMPLE 4

The following example shows that BCR destabilization requires receptor aggregation and protein-tyrosine kinase activation.

Figure 4A:
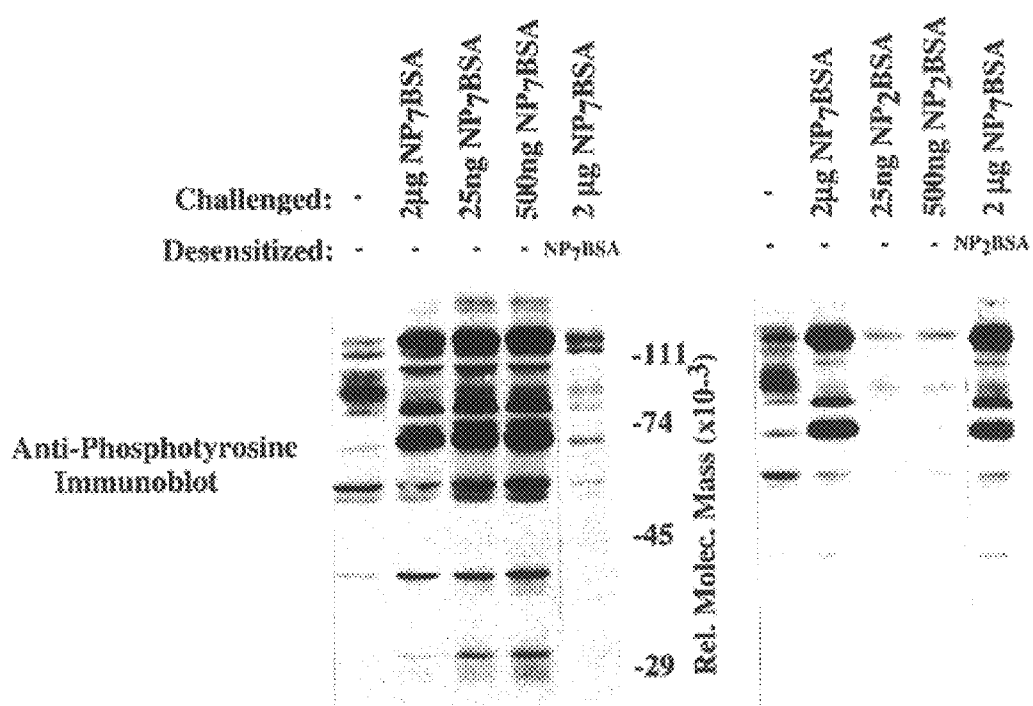
FIG. 4A is a digitized image showing an anti-phosphotyrosine immunoblot of K46μ cells desensitized with NP$_7$BSA or NP$_2$BSA.

To further define the relationship between BCR destabilization and receptor desensitization it was determined whether low valency antigen is capable of mediating these effects. FIG. 4A shows an anti-phosphotyrosine immunoblot of K46μ cells desensitized with NP$_7$BSA (left panel, lane 5) or NP$_2$BSA (right, lane 5). Unstimulated cells (lane 1 of each panel), cells stimulated with challenge dose of NP$_7$BSA (2 μl/5×10$^6$ cells/0.1 ml; lane 2 of each panel), cells stimulated with desensitizing dose (25 ng/5×10$^6$ cells/ml); lane 3 panel: NP$_7$BSA, lane 3 right panel: NP$_2$BSA), cells stimulated with 500 ng/5×10$^6$ cells/ml; lane 4 left panel: NP$_7$BSA, lane 4 right panel: NP$_2$BSA), cells desensitized with 25ng/5×10$^6$ cells/ml NP$_7$BSA for 2 hours then challenged with 2 μg/5×10$^6$ cells/0.1 ml NP$_7$BSA (lane 5 of each panel). As shown in FIG. 4A, high (NP$_7$BSA) but not low (NP$_2$BSA) valency antigens induced receptor desensitization (lane 5 compared to lane 2 of each panel).

Figure 4B:
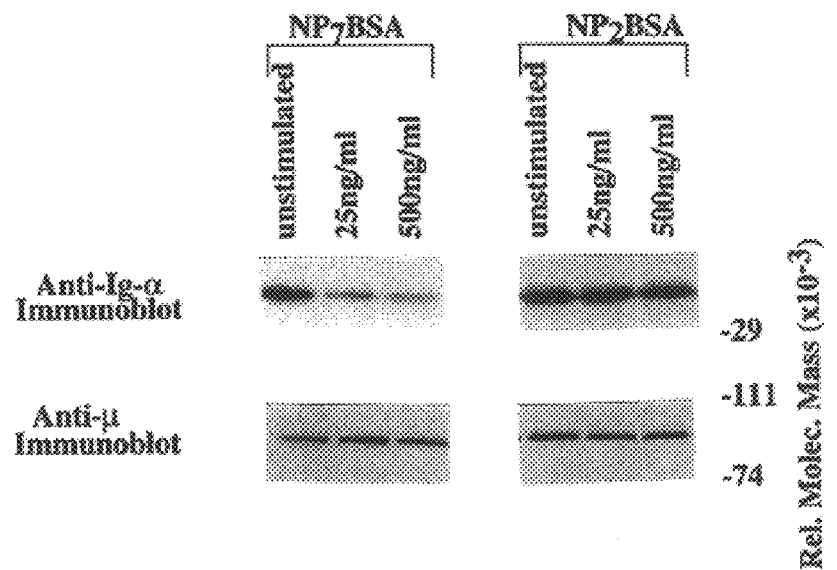
FIG. 4B is a digitized image showing anti-Ig-α and anti-μ immunoblots of IgM immunoprecipitates from unstimulated cells and cells stimulated with two doses of either NP$_7$BSA or NP$_2$BSA.

FIG. 4B shows anti-Ig-α and anti-μ immunoblots of IgM immunoprecipitates from unstimulated cells (lane 1 of each panel) and cells stimulated with two doses of either NP$_7$BSA or NP$_2$BSA; 25 ng/5×10$^6$ cells/ml (lane 2 of each panel), 500ng/5×10$^6$ cells/ml (lane 3 of each panel). As shown in FIG. 4B upper left, NP$_7$BSA induced dissociation of Ig-α/Ig-β from mIgM at an antigen dose that induced receptor desensitization (25 ng/ml) and at a higher antigen dose (500 ng/ml). In contrast, NP$_2$BSA did not induce tyrosine phosphorylation or receptor desensitization (FIG. 4A), and was unable to induce BCR destabilization (FIG. 4B upper right). These results show that only antigens of sufficiently high valence to induce receptor desensitization also induce BCR destabilization.

EXAMPLE 5

The following example demonstrates that inhibition of receptor-mediated Syk and Lyn activation prevent BCR destabilization.

Figure 5A:
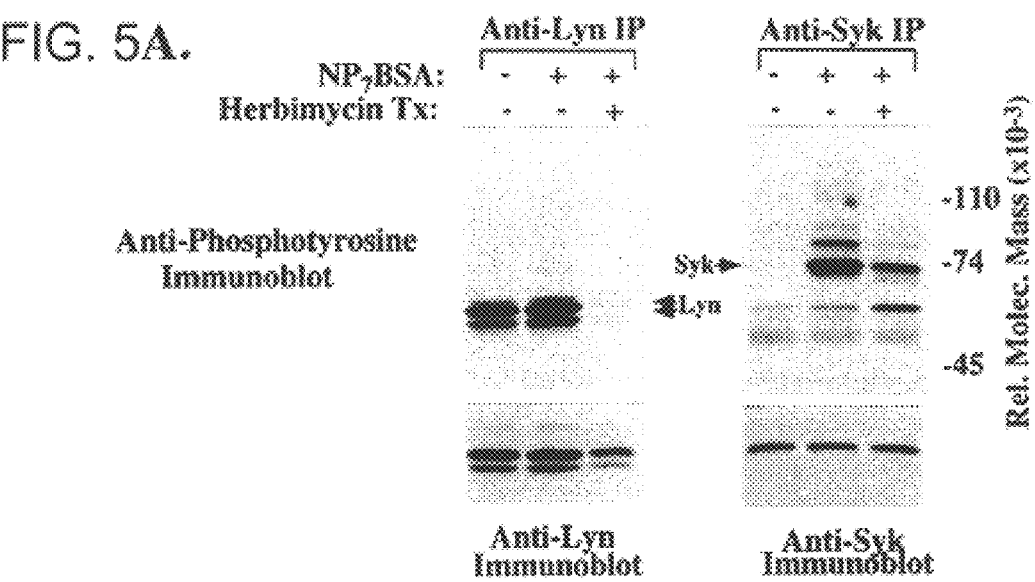
FIG. 5A is a digitized image showing anti-phosphotyrosine immunoblots of anti-Lyn or anti-Syk immunoprecipitates.
Figure 5B:
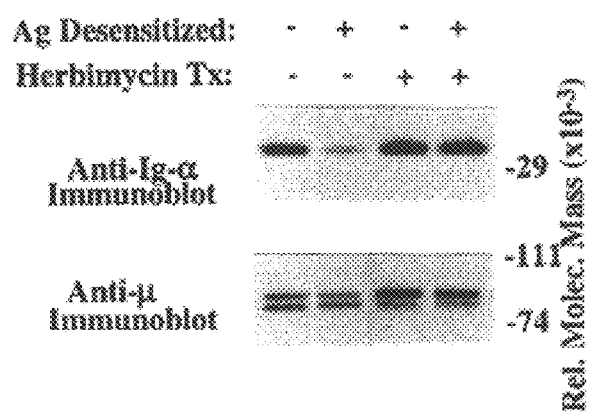
FIG. 5B is a digitized image showing anti-Ig-α and anti-μ immunoblots of IgM immunoprecipitates from unstimulated cells, cells stimulated with antigen for 2 hours, cells that were herbimycin treated but unstimulated, and cells that were herbimycin treated and antigen stimulated for 2 hours.

The above data suggest that receptor aggregation and/or activation of a specific protein tyrosine kinase cascade is responsible for the BCR destabilization. To address whether signal transduction is required for receptor destabilization, the activation of protein tyrosine kinases, Lyn and Syk, were inhibited with the pharmacological agent, herbimycin. FIG. 5A shows inhibition of protein tyrosine kinases prevents BCR destabilization. In this figure, anti-phosphotyrosine immunoblots of anti-Lyn (left panel) or anti-Syk (right panel) immunoprecipitates are shown. K46μ cells were either untreated (lane 1 and 2 of each panel) or herbimycin treated (lane 3 of each panel) then stimulated with NP$_7$BSA (500 ng/5×10$^6$ cells/ml) to assess BCR sensitivity. The membrane was then stripped and reprobed with anti-Lyn and anti-Syk, respectively, to assess protein levels. FIG. 5B shows anti-Ig-α and anti-μ immunoblots of IgM immunoprecipitates from unstimulated cells (lane 1), cells stimulated with antigen for 2 hours (lane 2), cells that were herbimycin treated but unstimulated (lane 3) and cells that were herbimycin treated, and antigen stimulated for 2 hours (lane 4). The levels of μ-heavy chain from each immunoprecipitate are shown in the anti-μ immunoblot. As shown in FIG. 5A, antigen stimulation of cells in the absence of herbimycin led to tyrosine phosphorylation of Syk and Lyn (lane 1 and 2 of each panel) while herbimycin treatment completely inhibited Lyn tyrosine phosphorylation (left panel, compare lane 2 to lane 3) and partially inhibited Syk phosphorylation (right panel, compare lane 2 to lane 3). To test the ability of antigen to induce BCR destabilization in the absence of Lyn activation, we analyzed immunoprecipitated BCR complexes from cells that had been herbimycin treated prior to antigen stimulation. The data in FIG. 5B, show that antigen does not induce receptor destabilization in herbimycin treated cells. These results indicate that dissociation of Ig-α/Ig-β from mIg requires protein tyrosine kinase activation.

EXAMPLE 6

The following example demonstrates that BCR destabilization requires a specific signal through the BCR.

Figure 5C:
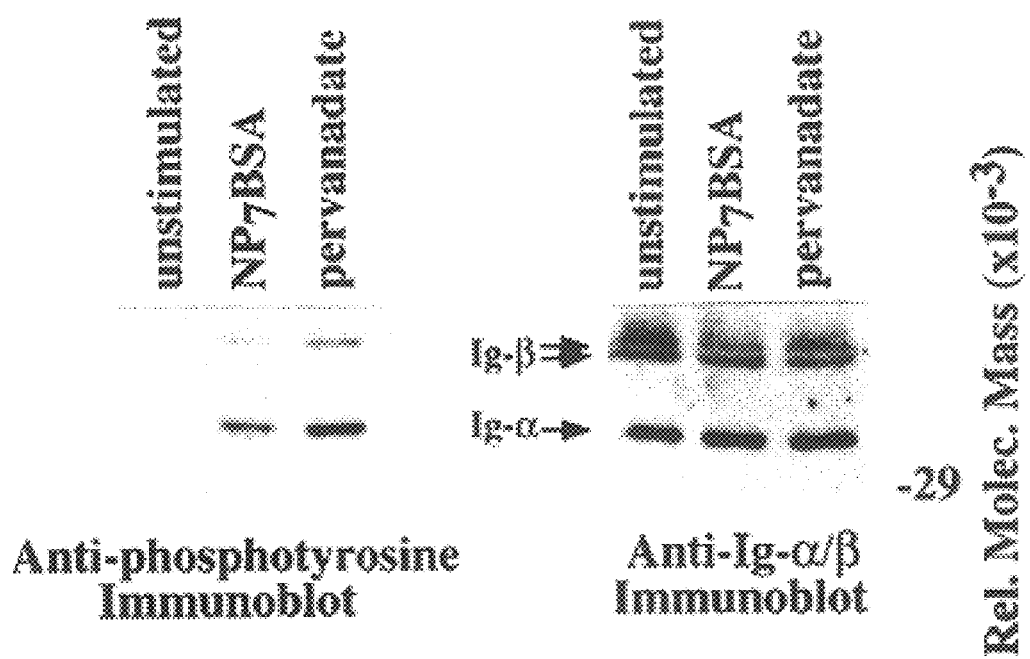
FIG. 5C is a digitized image showing anti-phosphotyrosine immunoblot of anti-Ig-α immunoprecipitation.
Figure 5D:
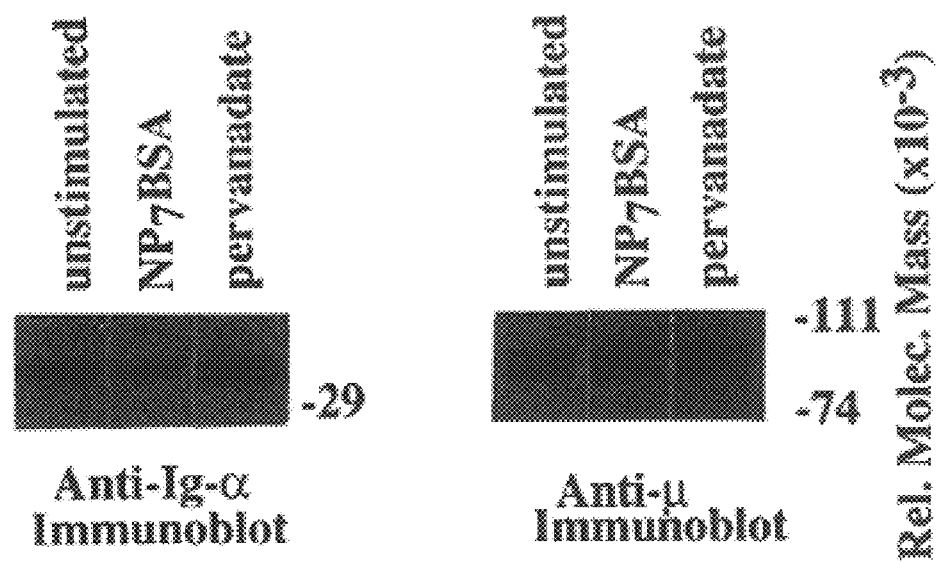
FIG. 5D is a digitized image showing anti-Ig-α and anti-μ immunoblots of IgM immunoprecipitates.

To assess whether tyrosine phosphorylation of cellular proteins was sufficient to induce uncoupling, cells were treated with pervanadate to induce tyrosine phosphorylation by inhibition of phosphatases. To assess the ability of pervanadates to induce phosphorylation of effectors involved in BCR signal transduction, Ig-α/Ig-β were immunoprecipitated at levels comparable to antigen treated cells. To determine if this alone was sufficient to induce uncoupling, the amount of Ig-α/Ig-β in anti-β immunoprecipitates was analyzed. FIGS. 5C and 5D show dissociation of the mIg from Ig-α/Ig-β requires a specific signal through the BCR. FIG. 5C (left panel) shows anti-phosphotyrosine immunoblot of anti-Ig-α immunoprecipitation. Unstimulated cells (lane 1), cells treated with $NP_7BSA$ (2 μg/$5 \times 10^6$ cells/0.1 ml)(lane 2), and cells treated with pervanadate (lane 3). FIG. 5C (right panel) shows that the membrane was stripped then sequentially blotted for Ig-α and Ig-β. FIG. 5D shows anti-Ig-α (left panel) and anti-β (right panel) immunoblots of IgM immunoprecipitates. Unstimulated cells (lane 1), $NP_7BSA$ (2μg/$5 \times 10^6$ cells/0.1 ml) stimulated cells (lane 2), and pervanadate treated cells (lane 3). As shown in FIG. 5D, pervandadatc-induced tyrosine phosphorylation did not result in destabilization of the BCR complex (lane 2 and 3 compared to lane 1). It can not be ruled out, however, that pervanadate treatment may not induce the same pattern of tyrosyl phosphorylation as antigen and therefore may be unable to promote receptor destabilization. These data show that the pervanadate-induced phosphorylation of Ig-α and Ig-β is not a sufficient "signal" to propagate destabilization of the BCR.

EXAMPLE 7

The following example shows that antigen-induced BCR destabilization occurs on the cell surface.

Figure 6A:
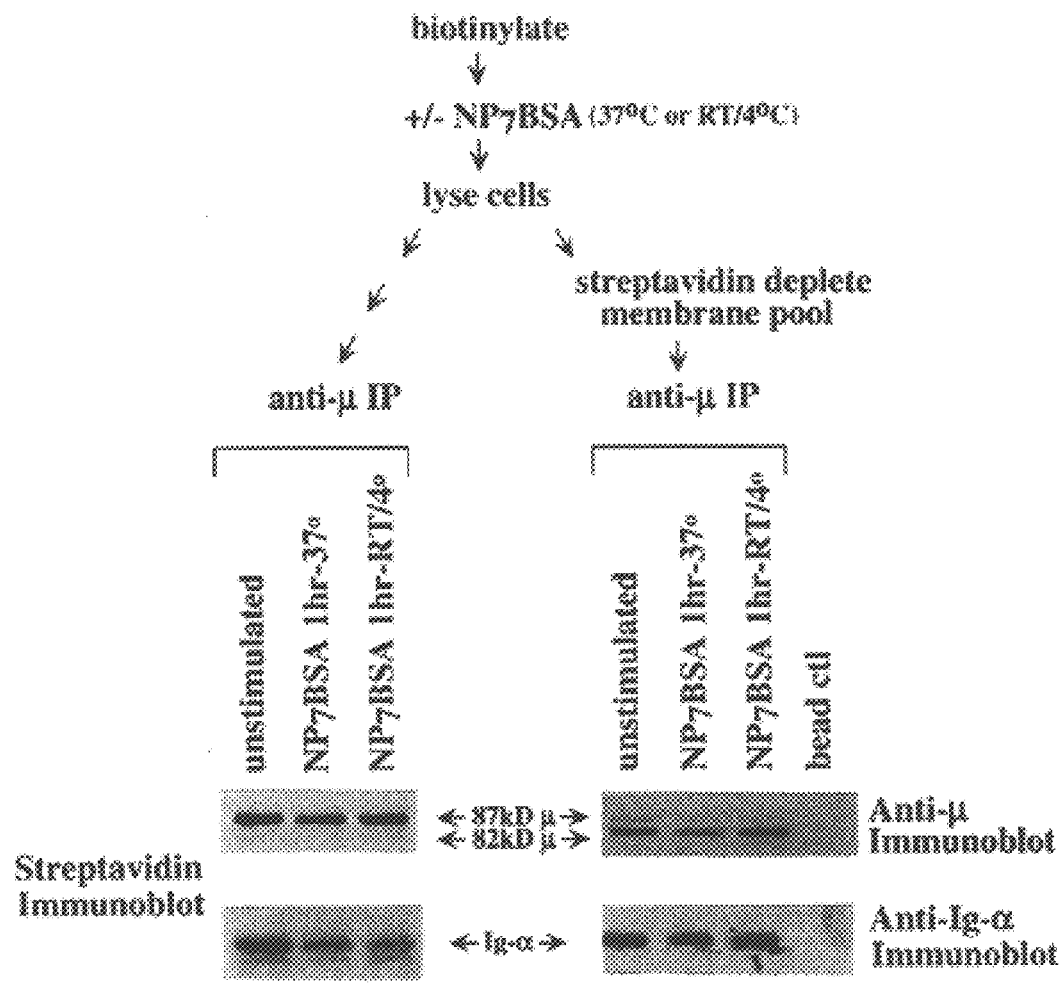
FIG. 6A is a digitized image showing the schematic representation of the experimental design and a streptavidin immunoblot of an anti-μ immunoprecipitate from biotinylated cells.

To ascertain whether receptor destabilization occurs on the cell surface, we utilized cell surface biotinylation to track the cell surface receptor pool. Cells were surface biotinylated then stimulated with antigen to induce BCR destabilization (see schematic FIG. 6A). Streptavidin immunoblotting of receptor immunoprecipitates revealed that indeed only the fully glycosylated (87 kD) pool of μ-chain was biotinylated and that the level of receptors did not significantly decrease following antigen stimulation (1 hour) regardless of the temperature of incubation (FIG. 6A lane 1–3). Most importantly, the levels of coprecipitated, biotin-tagged Ig-α decreased markedly following antigen stimulation indicating that the cell surface pool of BCR became destabilized. To assess whether the cytoplasmic receptor pool was also destabilized, we depleted the biotinylated surface pool by streptavidin immunoprecipitation, then immunoprecipitated remaining receptors with anti-μ (see schematic FIG. 6A). FIG. 6A is a schematic representation of the experimental design (above) and shows a streptavidin immunoblot of an anti-μ immunoprecipitate from biotinylated cells, as follows: unstimulated cells (lane 1), 37° C. stimulated cells (500 ng/$5 \times 10^6$/ml; lane 2) and RT/4° C. stimulated cells (500 ng/$5 \times 10^6$/ml); 15 min. at RT then 45 min. at 4° C.; lane 3) lower right: anti-μ or anti-Ig-α immunoblot of biotin-depleted receptors. Unstimulated cells (lane 1), 37° C. stimulated cells (500 ng/$5 \times 10^6$/ml; lane 2) and RT/4° C. stimulated cells (500 ng/$5 \times 10^6$/ml; 15 min at RT then 45 min at 4° C.; lane 3 ). Results show that only the partially glycosylated, 82 kD cytoplasmic form of μ remained following streptavidin depletion and, furthermore, the amount of coprecipiated Ig-α did not change following antigen stimulation (FIG. 6A lanes 4–6). These data confirm that only the membrane pool of BCR was destabilized following receptor engagement.

Figure 6B:
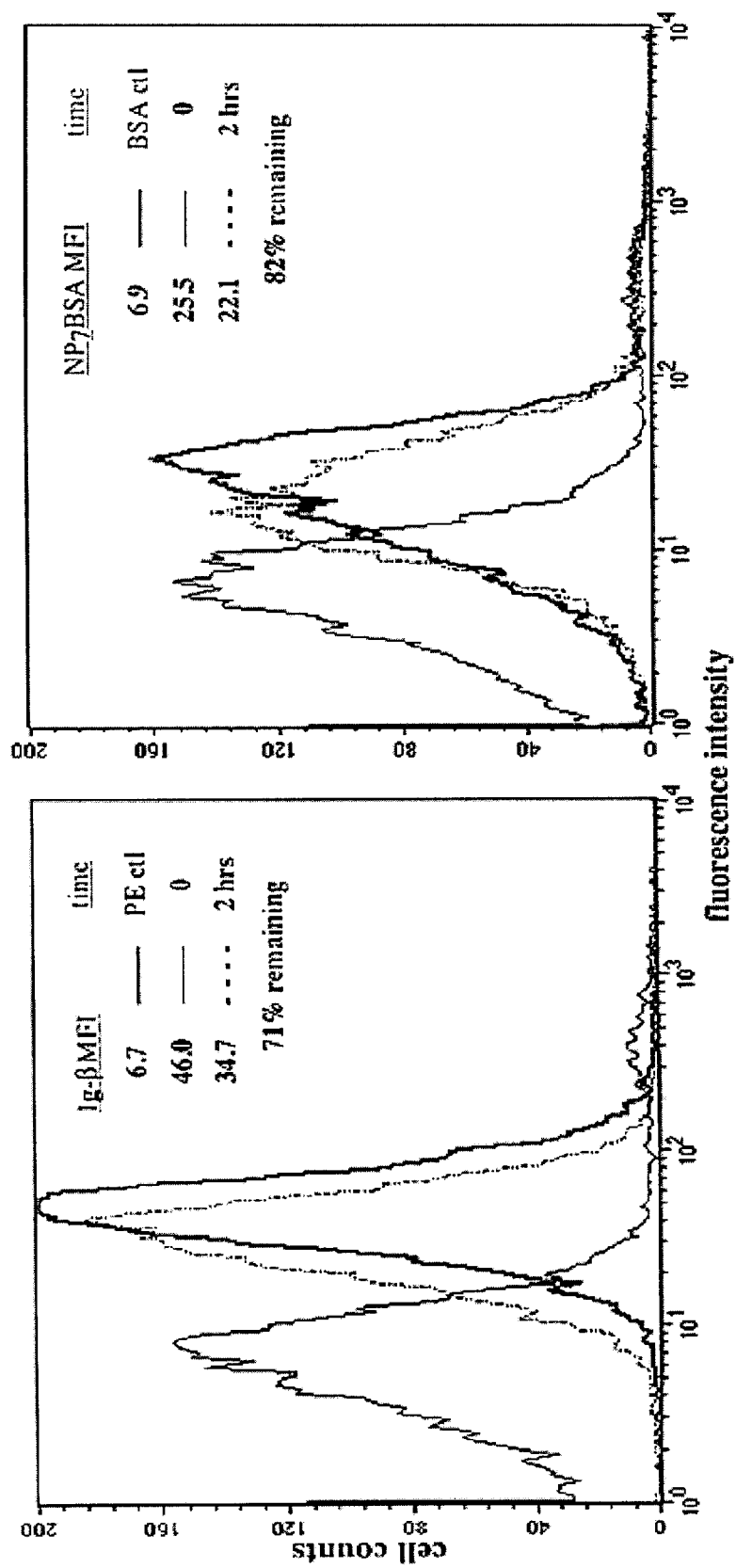
FIG. 6B is a graph showing surface staining with anti-Ig-β or NP$_7$BSA.

To address whether the destabilized BCR components remained on the cell surface the levels of surface Ig-β and the antigen binding receptors were measured by flow cytometric analysis. FIG. 6B shows that desensitized cells maintain surface Ig-β and antigen binding BCR. Specifically, FIG. 6B shows surface staining with anti-Ig-β (left panel) or $NP_7BSA$ (right panel) of antigen desensitized cells. The solid black line represents staining of naive cells treated with phycoerythrin-streptavidin (left panel) or biotinylated BSA (right panel). The heavy line of each panel represents naive cells stained 10 minutes on ice with either Ig-β (left panel) or the challenge dose of $NP_7BSA$ (2 μg/$5 \times 10^6$/cells/0.1 ml; right panel). The dotted line represents Ig-β staining (left panel) or $NP_7BSA$ staining (2μg/$5 \times 10^6$/cells/0.1 ml; right panel) of cells desensitized 2 hours with $NP_7BSA$ (25 ng/$5 \times 10^6$/cells/ml). Median fluorescence intensity (MFT) of each population is indicated in the upper right of each panel. As shown in FIG. 6B, antigen treated cells retained approximately 71% of their surface Ig-β and 82% of antigen binding capability compared to untreated cells. Considered in view of the 80% reduction in mIg associated Ig-α/Ig-μ, this indicates that destabilization of the BCR components must occur on the cell surface.

EXAMPLE 8

The following example shows that the Ig-α/Ig-β dimers remain competent to transduce signals in antigen desensitized cells.

Figure 7:
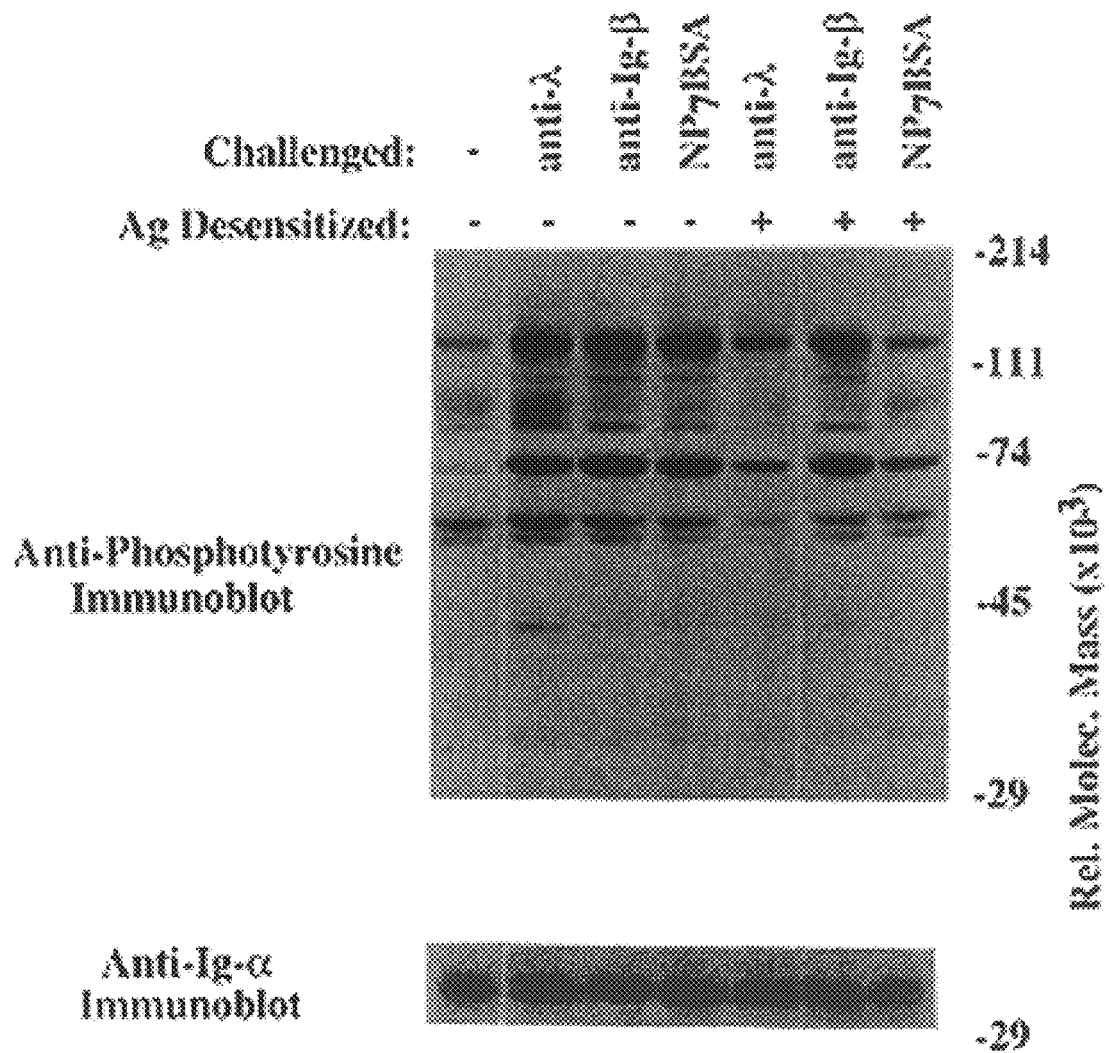
FIG. 7 is a digitized image showing that desensitized cells remain competent to signal through Ig-β.

Our previous findings shows that although neither receptors nor Lyn is tyrosine phosphorylated following challenge of desensitized cells. Receptor-associated Lyn isolated from these cells can be activated by binding to doubly phosphorylated ITAM peptides (Vilen et al., 1997). This suggests that the effector molecules involved in BCR signaling are functional in desensitized cells but that an early step in receptor activation is defective. Taken together with the present results, the present inventors believe that desensitization reflects failed transduction of signals from mIg to Ig-α/Ig-β and hence to downstream effectors. If this is the case, Ig-α/Ig-β dimers on the surface of desensitized cell should remain competent to transduce signals. To test whether these Ig-α/Ig-β subunits remained competent to signal when aggregated, it was determined whether the monoclonal anti-Ig-β antibody HM79 induces signal transduction in antigen desensitized cells. FIG. 7 (upper) shows an anti-phosphotyrosine immunoblot of naive K46μ cells (lanes 1–4) or K46μ cells desensitized 2 hours with $NP_7BSA$ (25 ng/$5 \times 10^6$cells/ml; lanes 5–7) that were challenged with either anti-λ (2 μg/$5 \times 10^6$/cells/0.1 ml; lanes 2 and 5), and anti-Ig-β (1 μg/$5 \times 10^6$/cells/0.1 ml; lanes 3 and 6) or high dose of $NP_7BSA$ (2 μg/$5 \times 10^6$/cells/0.1 ml; lanes 4 and 7). The portion of FIG. 7 shows the membrane stripped and reprobed with anti-Ig-α to reveal loading differences. As shown in FIG. 7, K46μ cells desensitized with antigen remained responsive to anti-β (lane 3 compared to lane 6) but were unresponsive to high dose of antigen challenge (lane 4 compared to lane 7) or to anti-λ challenge (lane 2 compared to lane 5). These differences in tyrosine phosphorylation were not due to different amounts of protein whole cell lysate as evidenced by the Ig-α immunoblot. It is important to note that under the conditions used, cells retained cell surface levels of antigen binding mIg and Ig-β comparable to untreated cells. This result shows that although desensitized cells have destabilized surface BCR, the Ig-α/Ig-β signal transducing subunits remained competent to signal. These results indicate that destabilization of the BCR complex is at least in part responsible for the unresponsive state of desensitized receptors.

The data presented above show that receptor aggregation induces both desensitization and physical destabilization of the B cell antigen receptor. Destabilization was characterized by decreased association of Ig-α/Ig-β dimers with mIg. Both BCR destabilization and receptor desensitization occur with 15–30 minutes following receptor ligation and both require receptor aggregation and protein tyrosine kinase activation. The signal to destabilize the BCR is receptor-specific, since enhancement of protein tyrosine phosphorylation by inhibition of phosphatases does not induce this event, despite inducing quantitatively similar levels of effector phosphorylation compared to antigen. Furthermore, antigen desensitized cells remain competent to signal through the transducer subunit(s), indicating that desensitization is caused by failure to transmit signals to the Ig-α/Ig-β transducer complex following antigen binding to mIgM. Taken together, these data show that receptor destabilization plays a role in mediating the unresponsiveness of antigen desensitized and perhaps anergic B cells.

Physical dissociation of receptor/transducer complexes has been previously described in T cells. The T cells receptor-CD3 complex (TCR-CD3) is composed of TCR-α/β or γ/δ, and the associated CD3 complex, composed of γ,δ, and ε and dimers of the TCR-ζ family proteins (ζ and η). In response to anti-CD3 ligation, the TCR-α/β is modulated from the cell surface with no effect on surface expression of the CD3ε complex (Kishimoto et al., 1995). Similarly, CD3ζ was shown to exhibit a half life distinct from that of the rest of the TCR subunits (Ono et al., 1995). These results revealed a physical dissociation of the TCR complex following receptor ligation, however, a direct extrapolation of these experiments to the B cell (i.e., ligation of Igα or Igβ) resulted in BCR signaling. Therefore, prior to the present invention, there was no indication that such a physiologic dissociation following receptor ligation would be characteristic of other multisubunit antigen receptors, such as the B cell antigen receptor, pre-B cell receptor, pro-B cell receptor and Ig FcR.

The data disclosed herein provide an unexpected explanation for previous studies showing that in receptor desensitized cells, downstream kinases can be activated pharmacologically, and that the defect maintaining desensitized cells in the unresponsive state lies at the level of the receptor (Vilen et al., 1997). The data presented here show that stimulation of desensitized cells with anti-Ig-β results in signal transduction indicating that the unresponsiveness of desensitized receptors reflects failure to transmit "signals" from mIg to Ig-α/Ig-β dimers. It is also possible that another pool of surface Ig-α/β that are not desensitized in "trans" by BCR ligation contribute to signal transduction through Ig-β.

Without being bound by theory, there are two possible mechanisms of action for the receptor dissociation discovered by the present inventors. First, it is possible that all cell surface BCR are actually destabilized, and thus desensitized, and second, it is possible that a proportion of mIg that continue to co-precipitate with Ig-α/Ig-β remain signal competent. If the latter is true, data suggest that when diluted in an excess (60–80%) of destabilized receptors, these "competent" BCR cannot achieve the signal threshold. Although it remains to be formally proven that the density of the competent receptors on desensitized cells is sufficiently low to prevent renewed receptor aggregation and signaling, extrapolation of the present data to studies in T cells suggest that the absolute receptor number is critical in defining sensitivity to antigen. Reducing the T cell receptor surface density as little as 35% resulted in a disproportionate increase in the amount of antigen required to reach the activation threshold (Viola and Lanzavecchia, 1996). Measuring the effect of changes in the surface TCR density was achieved by ligand binding and subsequent receptor down-modulation, a process that required several days. In the BCR destabilization model, such a consequence can be achieved within 15–30 minutes, prior to receptor down-modulation. This early post-stimulation effect provides a mechanism of rapidly reducing the numbers of functional BCR by inactivating most receptors by destabilization of the receptor complex.

The in vitro model of receptor desensitization used in this study is based on reports of desensitization of surface receptors with a dose of antigen that was titrated to give maximum $Ca^{2+}$ mobilization and maximum inductive tyrosine phosphorylation. An antigen dose of 25 ng/$5 \times 210^6$ cells/ml occupies only 25% of the total cell surface receptors allowing challenge of these cells by antigen ligation of the remaining receptors. Because the affinity of NP for this receptor is moderate ($K_D = 5/10^6$) it is not clear whether the inbound receptors have been bound by antigen which then dissociated. However, staining cells with biotinylated antigen following desensitization revealed that although they remained unresponsive, 70% of the original cell surface receptors remain competent to bind antigen upon challenge (Vilen et al., 1997). Therefore, the dependence of desensitization on receptor occupancy has been difficult to assess. Without being bound by theory, the present inventors believe that, with reference to the data in FIG. 2C and FIG. 4, it is most likely that the destabilization of the BCR requires ligation of only a small proportion of receptors, as a dose of antigen known to occupy 25% of receptors, induces desensitization and destabilization. However, the possibility can not be excluded that at low antigen doses, serial engagement of all receptors is necessary for the destabilization and desensitization described herein. Attempts to eliminate the serial receptor engagement caveat using higher affinity receptor/antigen systems (such as the anti-HEL transgenic mouse) have been inconclusive due to rapid movement of receptor to the detergent insoluble fraction following aggregation (FIG. 1 panel 4).

The failure to rapidly down-modulate receptors following antigen binding in both the K46μ lymphoma and the 3–83 μδ splenic B cells (FIGS. 1 and 3) is consistent with the ability to immunoprecipitate equal amounts of mIgM from unstimulated and stimulated cells, but is in contrast to previous observations that anti-receptor antibody ligation stimulates capping and endocytosis of receptors (Albrecht and Noelle, 1988; Braun et al., 1982; Goroff et al., 1986; Woda and McFadden, 1983; Woda and Woodin, 1984). Data described here indicate that this different behavior results from different affinity of antigen for its receptor. Earlier studies addressing attachment of mIgM to cytoskeletal consistently used anti-receptor antibodies of high affinity. In the present studies, movement of antigen bound receptors to the detergent insoluble fraction, coincident with loss from the cell surface, was seen only after prolonged periods of moderate affinity antigen binding (>3 hrs) but rapidly following high affinity anti-receptor antibody binding to BCR (Vilen and Cambier; unpublished observation and FIG. 1 panel 4). Affinity dependence of the response may explain the apparent inconsistency between the present inventor's data and that published by Jugloff and Jongstra-Bilen, which showed ligand-induced Ig-α translocation to the membrane skeleton as part of the BCR complex (Jugloff and Jongstra-Bilen, 1997). It is unclear if the rate at which receptors move into membrane rafts is also a function of ligand affinity. It is noteworthy that studies to date have employed only high affinity interactions (anti-TCR and DNP-IgE/Fcε/R1) to demonstrate ligand-induced receptor movement to rafts or detergent-resistant membrane domains (Field et al., 1997; Xavier et al., 1998; Zhang et al., 1998). Clearly, moderate affinity antigens (NP-$K_D$32 $1.5\times10^{-6}$ and 3–83 $ag1_{50}$Dex-$K_D$=approximately $10_{-5}$ to $10_{-6}$) represent a situation more pertinent to the interaction of B cells with antigen during the primary immune response.

The exact mechanism of Ig-α/Ig-β dissociation from mIg remains undefined. Previous studies have shown that the association of Ig-α/Ig-β with mIg involves interactions between the transmembrane domain and extracellular spacer of mIg with undefined regions of Ig-α/Ig-β. Two polar regions have been identified within the transmembrane region of mIg that mediate retention of mIg in the endoplasmic reticulum in the absence of Ig-α/IG-β association, and stabilize the interaction with Ig-α/Ig-β (reviewed in Campbell et al., 1994; Pao et al., 1997). Without being bound by theory, the present inventors believe that the rapidity of the induced stabilization of the BCR complex indicates that a post-translational event must mediate the separation of the transducer subunits from mIg (FIG. 2B). In addition, the present finding that protein tyrosine kinase activation is required for receptor destabilization indicates that activation of a specific kinase may facilitate the event (FIGS. 4 and 5A). Mechanistically, this could involve modification of Ig-α/Ig-β or residues within the transmembrane domain of mIg. However, it is also possible that modification of some other cell surface molecule mediates receptor destabilization. It is unlikely that the operative modification involves tyrosine phosphorylation of the receptor since no quantitative differences have been seen in anti-phosphotyrosine immunoblots of BCR components following receptor desensitization (Vilen and Cambier, unpublished data).

BCR destabilization may have important physiological functions in promoting a refractory period during T cell-B cell interactions and in maintaining the unresponsiveness of tolerant B cells. The binding of both self and foreign antigen to the BCR transmits an indistinguishable "first" signal, which by raising CD86 and MHC class II expression, primes the B cell for a productive interaction with $T_h$ cells. Whether the B cell becomes anergic or, alternatively, undergoes proliferation and differentiation is dependent on a "second" signal from an antigen-specific $T_h$ cell. One function of BCR destabilization may be to provide a refractory period while the B cell upregulates costimulatory molecules required for appropriate T cell interaction. This increased expression is transient, lasting 18–48 hours for CD86 and MHC class II, and interestingly CD86 can not be upregulated again by restimulation of anergic cells with antigen (Ho ct al., 1994).. This refractory period gives the cell a single opportunity to receive a "second" signal thereby providing a checkpoint that may ensure that autoreactive clones are not expanded. Thus, cells which were stimulated by antigen (signal 1) but fail to receive T cell help (signal 2) remain unresponsive and are destined to die (Hartley et al., 1993). Thus a second function of BCR destabilization may be to maintain autoreactive cells in an unresponsive state. Whether BCR destabilization is responsible for the long term unresponsiveness associated with anergy is unclear; however, such a mechanism would be consistent with the reported continuous need for antigen to maintain anergy (Vilen and Cambier, unpublished observation, Goodnow et al., 1991). The continuous presence of antigen may be required to destabilize newly synthesized receptors.

EXAMPLE 9

The following example demonstrates the production and characterization of antibodies which are capable of inducing receptor desensitization in B cells.

The above-described findings that antigen induced receptor desensitization is correlated with receptor destablilization suggested to the present inventors that receptor complexes may normally exist in an equilibrium between stable and unstable configurations. Further, since unstable receptors appear incompetent to signal, antibodies that trap the receptor in the unstable configuration may induce unresponsiveness to antigen. Such antibodies would be useful therapeutics for treatment of autoimmune diseases and could be used when immunosuppression is desired.

Therefore, to test the possibility that an antibody could serve as a compound for receptor desensitization, monoclonal antibodies against the extracellular domains of Igaα/Ig-β dimers were prepared and the ability of these antibodies to prevent antigen stimulation of calcium mobilizations, as an indication of signaling, was tested.

Production of Mouse Igα-Igβ Peptide cDNA encoding the extracellular domains (ECD) of mouse Igaα-Igβ were ligated into a baculovirus transfer vector containing a flag tag, which is a peptide sequence which allows eventual purification of the gene product. The transfer vector was used to make conal virus which was then used to infect SF9 cells. The SF9 cells expressed the Igα-Igβ ECD as a dimer that was subsequently purified over an anti-flag column.

Production of Monoclonal Antibody in Hamsters

Igα-Igβ ECD (50 ug), prepared as described above, was precipitated in alum and was injected intraperitoneally (i.p.) into an Armenian hamster. The hamster received two i.p. boosts of50 µg of the precipitated peptide spaced one month apart, and received a final boost 4 months later, seven days prior to the date of fusion of the hamster splenocytes with SP2/O (a mouse B cell myeloma parent cell line). The hamster was anaesthetized with $CO_2$, blood was drawn by cardiac puncture for positive control serum and the spleen was aseptically removed. A single cell splenocyte suspension was made and mixed with SP2/0 cells at a ratio of approximately 10:1. The combined cells were pelleted by centrifugation and subsequently were fused using 40% PEG (polyethylene glycol) 8000 wt./vol. The fused cells were washed in IMDM medium, gently resuspended in HAT medium (IMDM plus 10% fetal calf serum, glutamine, 2-mercaptoethanol, sodium pyruvate, penicillin-streptomycin, gentamicin, hypoxanthine, thymidine and aminopterin) containing $1\times10^4$/ml peritoneal exudate cells irradiated for 3000 rads from B10.D2 mice and were cultured in 96 well flat bottomed plates. Normal SP2/0 cells were also cultured in the HAT medium for control. The SP2/0 cells die in HAT medium whereas the hybrid cells survive. The resulting 264 cultures were maintained in IMDM and eventually weaned from the HAT medium (containing hypoxanthine, thymidine, aminopterin) over a 5 week period. Supernatants were collected for assay and cells were frozen and stored in liquid nitrogen for future use.

Assay of Hybrid Supernatants by ELISA

Supernatants were initially screened by sandwich ELISA using the Igα-Igβ ECD protein as a substrate. The substrate, at a 10 μg/ml dilution, was bound to a 96 well ELISA plate and washed. The supernatants were diluted 1:10, allowed to bind to the substrate and washed. The developing antibody used was Goat anti-Armenian Hamster IgG (H&L)-horseradish peroxidase at 1:50,000. Antibody reactivity was scored from 0–3 based on binding, with 3 being the highest score for binding. Thirty-three clones were reactive with the substrate in the ELISA. Fifteen of those clones were classified as 2 or 3 in reactivity and were selected for further characterization.

Purification of Antibody

Cells producing the selected antibodies were grown until >95% cell death was achieved in a 1–4 liter volume and supernatants were purified over protein A Sepharose columns. Two clones required purification over protein G Sepharose.

Staining of K46μ Cells with Hybrid Cell Antibody

Two separate staining experiments were done. In the first, K46μ cells (a mouse B lymphoma expressing an mIgM anti-nitrophenyl receptor)($0.5 \times 10^6$ per well in a 96 well plate) were incubated with 100λ of hybridoma antibody (b100 ug or 10 ug) for 30 minutes at 4° C. in staining medium (PBS+2% fetal calf serum+0.2% sodium azide). The plate was spun, cells washed in staining media and resuspended in 100 μl secondary antibody, Goat anti-Armenian hamster IgG (H&L)-FITC (1:500). The plate was incubated for 30 minutes at 4° C., spun, cells washed in staining media and resuspended for FACS analysis. Two of the hybrid clones were positive (#172 and #32) with clone #172 being more positive than clone #32.

In the second experiment, the hybridoma antibody concentration was not standardized due to limited quantity. The protein concentration of the antibodies tested were 0.419 mg/ml (#32) and 1 mg/ml (#172). K46 μg were seeded at $1.66 \times 10^6$ per 2ml in IMDM and cultured overnight (20 hours) with either no added antibody or 1:10 final concentration of each antibody tested. Therefore, cells in the overnight experiment were incubated with 100 μg/ml of #172 and 41.9 μg/ml of #32. Approximately $0.5 \times 10^6$ cells were removed from each culture into a 96 well plate, spun, cells washed with staining media and then resuspended in 100λ secondary antibody (see paragraph above). The plate was incubated for 30 minutes at 4° C., spun, cells washed in staining media and then resuspended for FACS analysis. Clones 172 and 32 both stained positively, but clone #32 showed the greatest increase in staining following 20 hour incubation. Cells (~200,000) were removed from each culture into a 96 well plate, spun, cells washed with staining media and then resuspended in 100λ b76-FITC 1:100 (anti-μ). The plate was incubated for 30 minutes at 4° C., spun, cells washed in staining media and then resuspended for FACS analysis.

Modulation of the receptors from the cell surface did not occur during the overnight incubation. Cells were also used from these overnight cultures for a calcium flux experiment.

Calcium Flux of K46μ cells with Hybrid Antibody

Figure 8:
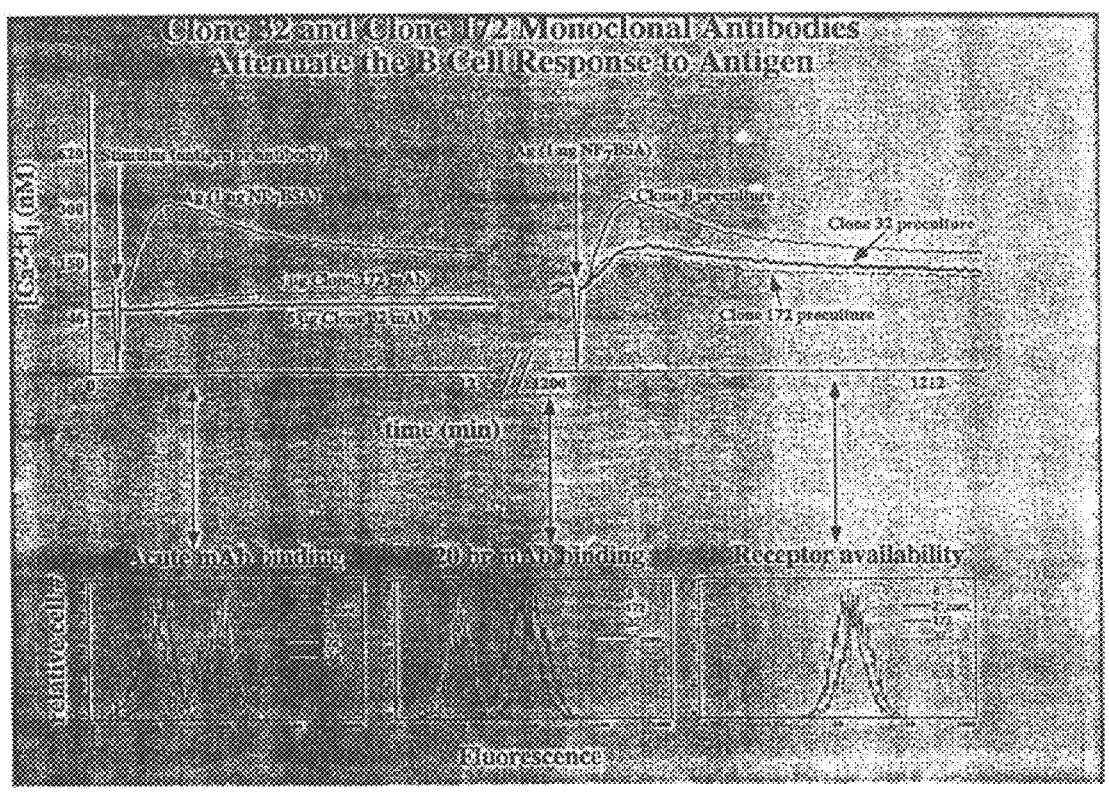
FIG. 8 is a graph showing that two antibodies of the present invention attenuate the B cell response to antigen.

K46μ cells were cultured overnight in the presence of 100μg/ml clone #172 or 41.9 μg/ml clone #32 antibody as above. These, as well as untreated K46μ cells were harvested and loaded with the calcium indicator Indo-1AM. Intracellular calcium concentrations were then monitored by flow cytometry before and after stimulation with 1 ng antigen (($NP_7$BSA)/$1 \times 10^6$ cells/ml). FIG. 8 shows the results of this experiment. Overnight culture with either clone #32 or clone #172 resulted in significant inhibition of antigen receptor-mediated calcium mobilization as compared with untreated cells. To examine the acute calcium responses of clones 32 and 172, untreated K46μ cells were stimulated with 5 μg of each antibody ($1 \times 10^6$ cells/ml). Stimulation with clone #172 resulted in a negligible response, while clone #32 induced no change in calcium concentration.

In summary, the results described above showed that two antibodies of 15 initially selected anti-Igα/βs blocked response to antigen but did not themselves stimulate the cells. These data support the present inventors' hypothesis that receptor complexes normally exist in an equilibrium between stable and unstable configurations and the conclusion that, since unstable receptors appear incompetent to signal, antibodies that trap the receptor in the unstable configuration can induce unresponsiveness to antigen. These antibodies, which, without being bound by theory, the present inventors believe will be immunosuppressive, will now be tested for the ability to block immune responses and to capture receptors in an unstable configuration as defined biochemically.

REFERENCES

Albrecht, D. L. and Noelle, R. J. (1988). Membrane Ig-cytoskeletal interactions. I.Flow cytofluorometric and biochemical analysis of membrane IgM-cytoskeletal interactions. J. Immunol. 141, 3915–22.

Braun, J., Hochman, P. S., and Unanue, E. R. (1982). Ligand-induced association of surface immunoglobulin with the detergent-insoluble cytoskeletal matrix of the B lymphocyte. J. Immunol. 128, 1198–204.

Brunswick, M., June, C. H., and Mond, J. J. (1994). B lymphocyte immunoglobulin receptor desensitization is downstream of tyrosine kinase activation. Cell. Immunol. 156, 240–4.

Cambier, J., Chen, Z. Z., Pasternak, J., Ransom, J., Sandoval, V. and Pickles, H. (1988). Ligand-induced desensitization of B-cell membrane immunoglobulin-mediated $Ca^2$+mobilization and protein kinase C translocation. Proc. Natl. Acad. Sci. USA 85, 6493–7.

Cambier, J. C. (1995). New nomenclature for the Reth motif (or ARH1/TAM/ARAM/YXXL) [letter]. Immunol. Today 16, 110.

Cambier, J. C., Fisher, C. L., Pickles, H., and Morrison, D. C. (1990). Dual molecular mechanisms mediate ligand-induced membrane Ig desensitization. J. Immunol. 145, 13–9.

Campbell, K. S., Backstrom, B. T., Tiefenthaler, G., and Palmer, E. (1994). CART: a conserved antigen receptor transmembrane motif. Semin. Immunol. 6, 393–410.

Cooke, M. P., Heath, A. W., Shokat, K. M., Zeng, Y., Finkelman, F. D., Linsley, P. S., Howard, M. and Goodnow, C. C. (1994). Immunoglobulin signal transduction guides the specificity of B cell-T cell interactions and is blocked in tolerant self-reactive B cells. J.Exp.Med. 179, 425–38.

DeFranco, A. L. (1997). The complexity of signaling pathways activated by the BCR. Curr. Opin. Immunol. 9, 296–308.

Erikson, J., Radic, M. Z., Camper, S. A., Hardy, R. R., Carmack, C., and Weigert, M. (1991). Expression of anti-DNA immunoglobulin transgenes in non-autoimmune mice. Nature (Lond.) 349, 331–4.

Field, K. A., Holowka, D., and Baird, B. (1997). Compartmentalized activation of the high affinity immunoglobulin E receptor with membrane domains. J. Biol. Chem. 272, 4276–80.

Gay, D., Saunders, T., Camper, S., and Weigert, M. (1993). Receptor editing: an approach by autoreactive B cells to escape tolerance. J. Exp. Med. 177, 999–1008.

Goodnow, C. C., Brink, R., and Adams, E. (1991). Breakdown of self-tolerance in anergic B lymphocytes. Nature (Lond.) 352, 532–6.

Goodnow, C. C., Crosbie, J., Adelstein, S., Lavoie, T. B., Smith-Gill, S. J., Brink, R. A., Pritchard-Briscoe, H., Wotherspoon, J. S., Loblay, R. H., Raphael, K., et al. (1988). Altered immunoglobulin expression and functional silencing of self-reactive B lymphocytes in transgenic mice. Nature (Lond.) 334, 676–82.

Goodnow, C. C., Crosbie, J., Jorgensen, H., Brink, R. A., and Basten, A. (1989). Induction of self-tolerance in mature peripheral B lymphocytes [see comments]. Nature (Lond.) 342, 385–91.

Goroff, D. K., Stall, A., Mond, J. J. and Finkelman, F. D. (1986). In vitro and in vivo B lymphocyte-activating properties of monoclonal anti-delta antibodies. 1. Determinants of B lymphocyte activating properties. J. Immunol. 136, 2382–92.

Hartley, S. B., Cooke, M. P., Fulcher, D. A., Harris, A. W., Cory, S., Basten, A., and Goodnow, C. C. (1993). Elimination of self-reactive B lymphocytes proceeds in two stages; arrested development and cell death. Cell 72, 325–35.

Hertz, M. and Nemazee, D. (1997). BCR ligation induces receptor editing in IgM-IgD-bone marrow B cells in vitro. Immunity 6, 429–36.

Ho, W. Y., Cooke, M. P., Goodnow, C. C., and Davis, M. M. (1994). Resting and anergic B cells are defective in CD28-dependent costimulation of naive CD4+ T cells. J. Exp. Med. 179, 1539–49.

Hombach, J., Tsubata, T., Leclercq, L., Stappert, H., and Reth, M. (1990). Molecular components of the B-cell antigen receptor complex of the IgM class. Nature (Lond.) 343, 760–2.

Johnson, S. A., Plieman, C. M., Pao, L., Schneringer, J., Hippen, K., and Cambier, J. C. (1995). Phosphorylated immunoreceptor signaling motifs (ITAMs) exhibit unique abilities to bind and activate Lyn and Syk tyrosine kinases. J. Immunol. 155, 4596–603.

Jugloff, L. S. and Jongstra-Bilen, J. (1977). Cross-linking of the IgM receptor induces rapid translocation of IgM-associated Ig alpha, Lyn, and Syk tyrosine kinases to the membrane skeleton. J. Immunol. 159, 1096–106.

Kim, K. J., Kannelopoulos-Langevin, C., Merwin, R. M., Sachs, D. H., and Asofsky, R. (1979). Establishment and characterization of BALB/c lymphoma lines with B cell properties. J. Immunol. 122, 549–54.

Kim, K. M., Alber, G., Weiser, P. and Reth, M. (1993). Signalling function of the B-cell antigen receptors. Immun. Rev. 132, 125–46.

Kishimoto, H., Kubo, R. T., Yorifuji, H., Nakayama, T., Asano, Y., and Tada, T. (1995). Physical dissociation of the TCR-CD3 complex accompanies receptor ligation. J. Exp. Med. 182, 1997–2006.

Koyama, M., Ishihara, K., Karasuyama, H., Cordell, J. L., Iwamoto, A., and Nakamura, T. (1997). CD79 alpha/CD79 beta heterodimers are expressed on pro-B cell surfaces without associated mu heavy chain. Int. Immunol. 9, 1767–72.

Kurosaki, T. (1997). Molecular mechanisms in B cell antigen receptor signaling. Curr. Opin. Immunol. 9, 309–18.

Lang, J., Jackson, M., Teyton, L., Brunmark, A., Kane, K. and Nemazee, D. (1996). B cells are exquisitely sensitive to central tolerance and receptor editing induced by ultralow affinity, membrane-bound antigen. J. Exp. Med. 184, 1685–97.

Nemazee, D. A. and Burki, K. (1989). Clonal deletion of B lymphocytes in a transgenic mouse bearing anti-MHC class I antibody genes. Nature (Lond.) 337, 562–6.

Okamoto, M., Murakami, M., Shimizu, A., Ozaki, S., Tsubata, T., Kumagai, S., and Honjo, T. (1992). A transgenic model of autoimmune hemolytic anemia. J. Exp. Med. 175, 71–9.

Ono, S., Ohno, H., and Saito, T. (1995). Rapid turnover of the CD3 zeta chain independent of the TCR-CD3 complex in normal T cells. Immunity 2, 639–44.

Pao, L., Carbone, A. M., and Cambier, J. C. (1997). Antigen Receptor Structure and Signaling in B cells. In Lymphocyte Signalling: Mechanisms, Subversions and Manipulation, M. M. Harnett and R.K.P., eds.: John Wiley & Sons Ltd.), pp. 3–29.

Rathmell, J. C., Townsend, S. E., Xu, J. C., Flavell, R. A., and Goodnow, C. C. (1996). Expansion or elimination of B cells in vivo: dual roles for CD40 and Fas (CD95)-ligands modulated by the B cell antigen receptor. Cell 87, 319–29.

Reth, M., Petrac, E., Wiese, P., Lobel, L., and Alt, F. W. (1987). Activation of V kappa gene rearrangement in pre-B cells follows the expression of membrane-bound immunoglobulin heavy chains. EMBO J. 6, 3299–305.

Russell, D. M., Dembic, Z., Morahan, G., Miller, J. F., Burki, K., and Nemazee, D. (1991). Peripheral deletion of self-reactive B cells. Nature (Lond.) 354, 308–11.

Sparks, A. B., Adey, N. B., Quilliam, L. A., Thorn, J. M., and Kay, B. K. (1995). Screening phage-displayed random peptide libraries for SH3 ligands. Meth. Enzymol. 255, 498–509.

Vilen, B. J., Famiglietti, S. J., Carbone, A. M., Kay, B. K., and Cambier, J. C. (1997). B cell antigen receptor desensitization: disruption of receptor coupling to tyrosine kinase activation. J. Immunol. 159, 231–43.

Viola, A., and Lanzavecchia, A. (1996). T cell activation determined by T cell receptor number and tunable thresholds [see comments]. Science 273, 104–6.

Woda, B. A., and McFadden, M. L. (1983). Ligand-induced association of rat lymphocyte membrane proteins with the detergent-insoluble lymphocyte cytoskeletal matrix. J. Immunol. 131, 1917–9.

Woda, B. A., and Woodin, M. B. (1984). The interaction of lymphocyte membrane proteins with the lymphocyte cytoskeletal matrix. J. Immunol. 133, 2767–72.

Xavier, R., Brennan, T., Li, Q., McCormack, C. and Seed, B. (1998). Membrane compartmentation is required for efficient T cell activation. Immunity 8, 723–32.

Zhang, W., Trible, R. P., and Samelson, L. E. (1998). LAT palmitoylation: its essential role in membrane microdomain targeting and tyrosine phosphorylation during T cell activation. Immunity 9, 239–46.

What is claimed is:

1. A method to desensitize a B cell antigen receptor, said method comprising: contacting a B cell antigen receptor with an antibody, wherein said B cell antigen receptor has a transducer component consisting of an Igα-Igβ dimer, and a membrane Ig (mIg) component, wherein said antibody binds to the extracellular domain of said transducer component;

wherein contact with said antibody: (1) causes a dissociation of said mIg component from said transducer component when said components are associated with each other prior to contact with said antibody; or (2) inhibits association of said mIg component with said transducer component when said components are dissociated from each other prior to contact with said antibody;

and wherein said B cell antigen receptor remains competent to bind its antigen, and fails, or has a reduced ability, to transduce signals.

2. The method of claim 1, wherein said antibody inhibits association of said mIg component with said transducer component when said components are dissociated from each other.

3. The method of claim 2, wherein said antibody selectively binds to a portion of said transducer component that contacts a portion of said mIg component when said receptor is bound by its natural antigen, thereby inhibiting contact of said transducer component with said mIg component.

4. The method of claim 2, wherein said antibody selectively binds to a portion of said transducer component which contacts a portion of said mIg component that is phosphorylated when said receptor is bound by its natural antigen, thereby inhibiting phosphorylation of said mIg component.

5. The method of claim 1, wherein said anti body is monovalent.

6. The method of claim 1, wherein said antibody is divalent.

7. A method to desensitize a B cell antigen receptor, wherein said B cell antigen receptor has a transducer component consisting of an Igα-Igβ dimer, and a membrane Ig (mIg) component, said method comprising contacting a B cell antigen receptor with a bi-specific antibody comprising:

a. a first portion which binds the extracellular domain of said transducer component of said B cell antigen receptor and: (1) causes a dissociation of said mIg component from said transducer component when said components are associated with each other prior to contact with said antibody; or (2) inhibits association of said mIg component with said transducer component when said components are dissociated from each other prior to contact with said antibody; and b. a second portion which selectively binds to a cell surface molecule expressed by a cell which expresses said B cell antigen receptor;

wherein said B cell antigen receptor remains competent to bind its antigen, and fails, or has a reduced ability, to transduce signals.

8. The method of claim 7, wherein said second portion binds to a cell surface molecule which is expressed by an autoreactive B cell.

9. The method of claim 7, wherein said second portion binds to an antigen binding region of said B cell antigen receptor.

10. The method of claim 1, wherein said mIg component is selected from the group consisting of IgO and IgM.

11. The method of claim 1, wherein said B cell antigen receptor selectively binds to an antigen associated with an autoimmune disease.

12. The method of claim 1, wherein said B cell antigen receptor selectively binds to an antigen associated with a graft cell.

13. The method of claim 1, wherein said B cell antigen receptor is expressed by a cell from the group consisting of an autoreactive B cell, a B cell comprising a B cell antigen receptor that selectively binds to an antigen on a graft, a B cell lymphoma and a chronic lymphocytic leukemia cell.

14. The method of claim 1, wherein said antibody is administered to a patient that has an autoimmune disease selected from the group consisting of rheumatoid arthritis, systemic lupus erythematosus, insulin dependent diabetes mellitis, multiple sclerosis, myasthenia gravis, Grave's disease, autoimmune hemolytic anemia, autoimmune thrombocytopenia purpura, Goodpasture's syndrome, pemphigus vulgaris, acute rheumatic fever, post-streptococcal glomeruonephritis,and polyarteritis nodosa.

15. The method of claim 1, wherein said antibody is administered to a patient by way of a therapeutic composition comprising a pharmaceutically acceptable carrier and said antibody.

16. The method of claim 15, wherein said therapeutic composition is administered in vivo.

17. The method of claim 15, wherein said therapeutic composition is administered ex vivo.

18. The method of claim 1, wherein said antibody is contacted with said B cell antigen in an in vitro assay.

* * * * *